United States Patent [19]

Betts et al.

[11] Patent Number: 5,527,791
[45] Date of Patent: * Jun. 18, 1996

[54] CARBAPENEM ANTIBIOTIC COMPOUNDS

[75] Inventors: Michael J. Betts, Wilmslow; Gareth M. Davies, Macclesfield, both of United Kingdom; Frederic H. Jung, Rilly la Montagne, France

[73] Assignee: Zeneca Limited, London, England

[*] Notice: The portion of the term of this patent subsequent to Oct. 26, 2014, has been disclaimed.

[21] Appl. No.: 123,998

[22] Filed: Sep. 21, 1993

[30] Foreign Application Priority Data

Sep. 28, 1992 [EP] European Pat. Off. .............. 92402648

[51] Int. Cl.⁶ ........................ C07D 487/04; A61K 31/40
[52] U.S. Cl. ............................................. 514/210; 540/350
[58] Field of Search ............................. 514/210; 540/350

[56] References Cited

U.S. PATENT DOCUMENTS

| 4,206,219 | 6/1980 | Christensen et al. . |
| 4,208,422 | 6/1980 | Christensen et al. . |
| 4,218,462 | 8/1980 | Christensen et al. . |
| 4,232,036 | 11/1980 | Christensen et al. . |

FOREIGN PATENT DOCUMENTS

| 0017992 | 10/1980 | European Pat. Off. . |
| 0126587 | 11/1984 | European Pat. Off. . |
| 0160391 | 11/1985 | European Pat. Off. . |
| 0182213 | 5/1986 | European Pat. Off. . |
| 0243686 | 11/1987 | European Pat. Off. . |
| 0443883 | 8/1991 | European Pat. Off. . |
| 0472062 | 2/1992 | European Pat. Off. . |
| 60-233076 | 11/1985 | Japan . |
| 9217481 | 10/1992 | WIPO . |

*Primary Examiner*—Rebecca Cook
*Attorney, Agent, or Firm*—Cushman Darby & Cushman

[57] ABSTRACT

The present invention provides a compound of the formula:

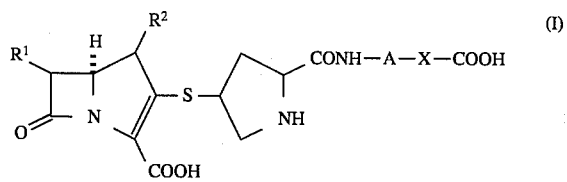

(I)

or a pharmaceutically acceptable salt or in vivo hydrolysable ester thereof wherein:

A is a group of the formula (IA) or (IB):

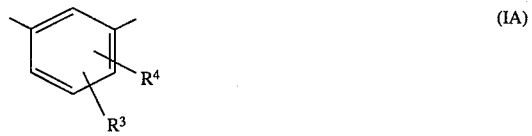

(IA)

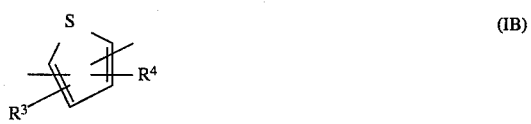

(IB)

$R^1$ is 1-hydroxyethyl, 1-fluoroethyl or hydroxymethyl;
$R^2$ is hydrogen or $C_{1-4}$alkyl;
$R^3$ and $R^4$ are the same or different and are a variety of substituents X is alkanediyl containing 1–6 carbon atoms optionally interrupted by O, $S(O)_x$ (wherein x is zero, one or two), —$CONR^5$— or —$NR^5$— or wherein $R^5$ is hydrogen or $C_{1-4}$alkyl;
or X is alkenediyl containing 1–6 carbon atoms optionally interrupted by O, $S(O)_x$ or —$NR^5$—.

8 Claims, No Drawings

CARBAPENEM ANTIBIOTIC COMPOUNDS

The present invention relates to carbapenems and in particular to such compounds containing a phenyl or thienyl ring substituted by a group bearing a carboxy function. This invention further relates to processes for their preparation, to intermediates in their preparation, to their use as therapeutic agents and to pharmaceutical compositions containing them.

The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

The present invention provides compounds with a broad spectrum of antibacterial activity including both Gram positive and negative, aerobic and anaerobic bacteria. They exhibit good stability to beta-lactamases. In addition representative compounds of this invention exhibit a very favourable duration of action.

The carbapenem derivatives referred to herein are named in accordance with the generally accepted semi-systematic nomenclature:

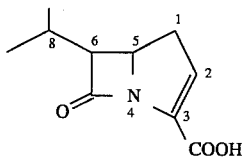

Accordingly the present invention provides a compound of the formula (I):

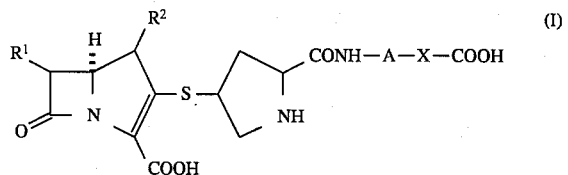

or a pharmaceutically acceptable salt or in vivo hydrolysable ester thereof wherein:

A is a group of the formula (IA) or (IB):

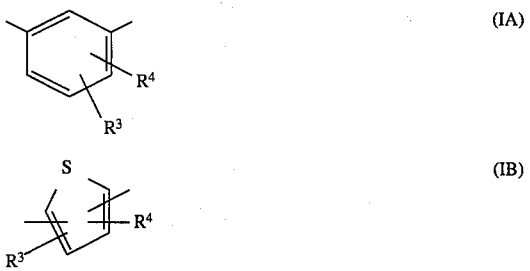

$R^1$ is 1-hydroxyethyl, 1-fluoroethyl or hydroxymethyl;

$R^2$ is hydrogen or $C_{1-4}$alkyl;

$R^3$ and $R^4$ are the same or different and are selected from hydrogen, halo, cyano, $C_{1-4}$alkyl, nitro, hydroxy, carboxy, $C_{1-4}$alkoxy, $C_{1-4}$alkoxycarbonyl, carbamoyl, $C_{1-4}$alkylcarbamoyl, di-$C_{1-4}$alkylcarbamoyl, trifluoromethyl, and $C_{3-4}$alkenyloxy: X is alkanediyl containing 1–6 carbon atoms optionally interrupted by O, $S(O)_x$ (wherein x is zero one or two), —$CONR^5$— or —$NR^5$— wherein $R^5$ is hydrogen or $C_{1-4}$alkyl;

or X is alkanediyl containing 2–6 carbon atoms optionally interrupted by O, $S(O)_x$ or —$NR^5$— wherein x and $R^5$ are as hereinbefore defined; with the provisos that:
i) the interrupting function ($O, S(O)_x, NR^5$, —$CONR^5$—) may be directly linked to the ring A, but is not directly linked to the —COOH function or to any carbon-carbon double bond in X; and
(ii) when the interrupting function is —SO— or —$SO_2$— it is not β to the COOH function or δ if there is an intervening carbon-carbon double bond in X.

Alkyl when used herein includes straight chain and branched chain substitutents for example methyl, ethyl, n-propyl, isopropyl, n-butyl and isobutyl.

In one aspect A is of the formula (IA). Preferably $R^1$ is 1-hydroxyethyl. $R^2$ is hydrogen or $C_{1-4}$alkyl for example methyl, ethyl, n-propyl, isopropyl or n-butyl. Preferably $R^2$ is hydrogen or methyl and in particular $R^2$ is methyl.

$R^3$ and $R^4$ are the same or different and are selected from hydrogen;

halo for example fluoro, bromo or chloro; cyano; $C_{1-4}$alkyl for example methyl, ethyl, n-propyl, isopropyl or n-butyl; nitro; hydroxy; carboxy;

$C_{1-4}$alkoxy for example methoxy or ethoxy; carbamoyl; $C_{1-4}$alkylcarbamoyl for example methylcarbamoyl or ethylcarbamoyl; di-$C_{1-4}$alkylcarbamoyl for example dimethylcarbamoyl or diethylcarbamoyl; trifluoromethyl;

and $C_{3-4}$alkenyloxy for example propen-1-yloxy.

In a particular aspect a suitable class of compounds is that in which $R^3$ and $R^4$ are the same or different and are selected from hydrogen, fluoro, chloro, hydroxy, carboxy, cyano, nitro, methyl, ethyl, methoxy, ethoxy, carbamoyl, methylcarbamoyl or dimethylcarbamoyl.

$R^3$ and $R^4$ may both be other than hydrogen but, in general, it is particularly preferred that at least one of $R^3$ and $R^4$ is hydrogen.

Particularly preferred compounds are those in which $R^3$ is hydrogen, hydroxy, methyl, methoxy, fluoro or chloro and $R^4$ is hydrogen.

In one aspect X is alkanediyl containing 1–6 carbon atoms, for example X is straight-chained $C_{1-4}$ alkylene such as methylene (—$CH_2$—), ethylene (—$CH_2CH_2$—) or trimethylene (—$CH_2CH_2CH_2$—). In another aspect X is a branched-chained moiety of 2–6 carbon atoms for example $C_{24}$ alkanediyl such as —$CH(CH_3)$—, —$CH(C_2H_5)$—, —$CH(CH_3)CH_2$—, —$C(CH_3)_2CH_2$—, —$CH_2CH(CH_3)$— or —$CH_2C(CH_3)_2$—.

In a further aspect X is alkanediyl containing 1–4 carbon atoms optionally interrupted by O, $S(O)_x$ wherein x is zero, one or two, $CONR^5$ or $NR^5$ wherein $R^5$ is hydrogen or $C_{1-4}$ alkyl; with the proviso that the interrupting function (O, $S(O)_x$, $CONR^5$, $NR^5$) is not immediately adjacent to the —COOH function, that is there is at least one carbon atom in the chain between the interrupting function and the terminal COOH group. The interrupting function may be directly linked to ring A.

Suitable values for X include —$SCH_2$—, —$SCH_2CH_2$—, —$S_2CH_2CH_2$—, —$OCH_2$—, —$OC(CH_3)_2$—, —$OCH_2CH_2$—, —$CH_2S$—$CH_2$—, —$CH_2OCH_2$, —$C(CH_3)_2$—O—$CH_2$—, —$CH_2$—O—$C(CH_3)_2$—, —$CONHCH_2$—, —$CH_2NHCH_2$— and —$CH_2N(CH_3)CH_2$—.

In yet a further aspect X is alkenediyl containing 2–6 carbon atoms for example —CH=CH—, —C(CH₃)=CH—, —CH=C(CH₃)—, —CH₂—CH=CH— and —CH=CH—CH₂—.

In another aspect X is alkenediyl containing 2–6 carbon atoms optionally interrupted by $O, S(O)_x$ or $NR^5$ for example —OCH₂CH=CH— or —SCH₂CH=CH—.

Typical values for X include methylene (—CH₂—), ethylene (—CH₂CH₂—), 1,1-dimethylmethylene (—C(CH₃)₂—), oxymethylene (—OCH₂—), oxyethylene (—OCH₂CH₂—), 1,1-dimethyloxymethylene (—OC(CH₃)₂—), methyleneoxymethylene (—CH₂OCH₂—), thiomethylene (—SCH₂—), vinylene (—CH=CH—), methylenecarbamoyl (—CONHCH₂—), 1-methylethenylene (—C(CH₃)=CH—), 2-methylethenylene (—CH=C(CH₃)—) and propene-1,3-diyl (—CH=CH—CH₂—) wherein, for the avoidance of doubt in all cases the atom at the left hand end of the depicted structure is linked to ring A and the atom at the right hand end of the depicted structure is linked to the carboxylic acid function.

Preferred values for X are methylene, ethylene, oxymethylene, vinylene, methyleneoxymethylene and thiomethylene.

In another aspect preferred values for X are methylene, ethylene, oxymethylene and vinylene.

The present invention covers all epimeric, diastereoisomeric and tautomeric forms of the compounds of the formula (I) wherein the absolute stereochemistry at the 5-position is as illustrated in formula (I). The compounds of the formula (I) have a number of other centres of optical activity, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring; and within the moiety X dependent on the structure thereof. Any carbon carbon-double bond present in X may be in either the E or Z configuration.

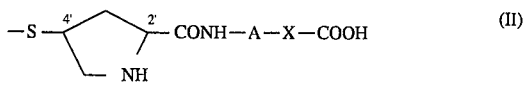

(II)

Preferred compounds are those in which the beta-lactam ring protons are in trans configuration with respect to one another. When $R^1$ is 1-hydroxyethyl or 1-fluoroethyl it is preferred that the 8-substituent has the R-configuration. Thus a preferred class of compounds is that of the formula (III):

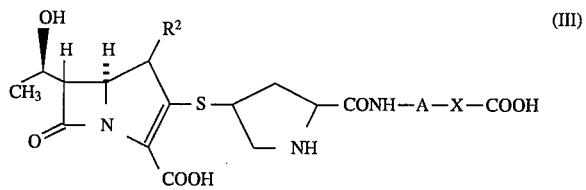

(III)

and pharmaceutically acceptable salts and in vivo hydrolysable esters thereof, wherein X, $R^2$ and A are as hereinbefore defined.

When $R^2$ is $C_{1-4}$alkyl for example methyl it is preferred that the compound is in the form of the 1R configuration.

Preferred compounds are those in which the pyrrolidine ring has the following absolute stereochemistry at the 2'- and 4'-positions:

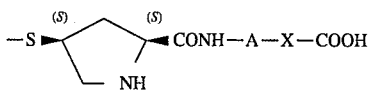

A preferred class of compounds of the present invention is that of the formula (IV):

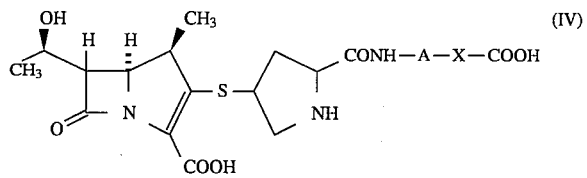

(IV)

and pharmaceutically acceptable salts and in vivo hydrolysable esters thereof wherein A and X are as defined hereinbefore in formula (I).

Another class of compounds of the present invention are those of the formula (IV) wherein A is of the formula (IA).

Particularly preferred compounds within the formula (IV) are those wherein $R^3$ and $R^4$ in A, are the same or different and are selected from hydrogen, fluoro, chloro, hydroxy, cyano, nitro, methyl, ethyl, methoxy, ethoxy, carbamoyl, methylcarbamoyl, dimethylcarbamoyl; and X is methylene, ethylene, oxymethylene, vinylene, methyleneoxy, methylene and thiomethylene.

Especially preferred compounds within the formula (IV) are those wherein $R^3$ is hydrogen; $R^4$ is hydrogen, hydroxy, methyl, methoxy, fluoro or chloro and X is oxymethylene or vinylene.

Suitable pharmaceutically acceptable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. For the avoidance of doubt the number of salt-forming cations may vary dependent on the number of carboxylic acid functions and the valency of said cations.

For the avoidance of doubt there may be one, two, three or four salt forming cations depending on the number of carboxylic acid functions and valency of said cations. In vivo hydrolysable esters are those pharmaceutically acceptable esters that hydrolyse in the human body to produce the parent compound. Such esters can be identified by administering, e.g. intravenously to a test animal, the compound under test and subsequently examining the test animal's body fluids. Suitable in vivo hydrolysable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy $C_{1-6}$alkyl esters for example 1-cyclohexyloxycarbonyloxyethyl; 1,3-dioxolen-2-onylmethyl esters for example 5-methyl-1,3-dioxolen-2onylmethyl; phthalidyl esters and $C_{1-6}$alkoxycarbonyloxyethyl esters for example 1-ethoxycarbonyloxyethyl and may be formed at any carboxy group in the compounds of this invention. Suitable in vivo hydrolysable esters for hydroxy include acetoxy, propionyloxy, pivaloyloxy, $C_{1-4}$alkoxycarbonyloxy for example ethoxycarbonyloxy, phenylacetoxy and phthalidyl.

Particular compounds of the present invention are:
(1R,5S,6S,8R,2'S,4'S)-2-(2-(3-(E- 2-carboxy-1-ethenyl)phenylcarbamoyl)-pyrrolidin- 4-ylthio)-6-(1-hydroxyethyl)-1-methylcarbapenem-3-carboxylic acid, (1R,5S,6S,8R,2'S,4'S)-2-(2-(3-(E- 2-carboxy-1-ethenyl)-6-hydroxy-phenylcarbamoyl)pyrrolidin- 4-ylthio)-6-(1-hydroxyethyl)-1-methylcarbapenem-3-carboxylic acid, (1R,5S,6S,8R,2'S,4'S)-2-(2-(3-carboxymethoxyphenylcarbamoyl)-pyrrolidin- 4-ylthio)-6-(1-hydroxyethyl)-1-methylcarbapenem-3-carboxylic acid, (1R,5S,6S,8R,2'S,4'S)-2-(2-(3-carboxyethylphenylcarbamoyl)pyrrolidin- 4-ylthio)-6-(1-hydroxyethyl)-1-methylcarbapenem-3-carboxylic acid, (1R,5S,6S,8R,2'S,4'S)-2-(2-(5-carboxymethyl- 2-hydroxyphenyl-carbamoyl)pyrrolidin- 4-ylthio)-6-(1-hydroxyethyl)-1-methylcarbapenem-3-carboxylic acid, (1R,5S,6S,8R,2'S,4'S)-2-(2-(3-carboxymethylphenylcarbamoyl)-pyrrolidin- 4-ylthio)-6-(1-hydroxyethyl)-1-methylcarbapenem-3-carboxylic acid, (1R,5S,6S,8R,2'S,4'S)-2-(2-( 3-carboxymethylaminocarbonylphenyl-carbamoyl)pyrrolidin- 4-ylthio)-6-(1-hydroxyethyl)-1-methylcarbapenem-3-carboxylic acid, (1R,5S,6S,8R,2'S,4'S)-2-(2-( 3-carboxymethoxymethylphenylcarbamoyl)-pyrrolidin- 4-ylthio)-6-(1-hydroxyethyl)-1-methylcarbapenem-3-carboxylic acid, (1R,5S,6S,8R,2'S,4'S)-2-(2-( 3-carboxymethylthiophenylcarbamoyl)-pyrrolidin- 4-ylthio)-6-(1-hydroxyethyl)-1-methylcarbapenem-3-carboxylic acid, (1R,5S,6S,8R,2'S,4'S)-2-(2-(2-carboxymethylcarbamoyl-5-thienyl-carbamoyl)pyrrolidin- 4-ylthio)-6-(1-hydroxyethyl)-1-methylcarbapenem-3carboxylic acid, and pharmaceutically acceptable salts and in vivo hydrolysable esters thereof.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids such as betamipron (also EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

| Composition 1 | |
|---|---|
| Compound of Example 1 | 50 mg |
| Composition 2 | |
| Compound of Example 1 | 50 mg |
| Glycine | 31 mg |

Further specific examples of compositions are as above, but where the compound of example 1 is replaced by any one of examples 2 to 10.

The pharmaceutical compositions of the invention will normally be administered to man in order to combat infections caused by bacteria, in the same general manner as that employed for imipenem due allowance being made in terms of dose levels for the potency of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V):

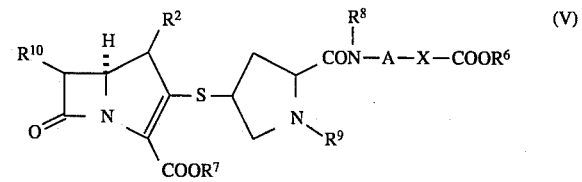

wherein A, X and $R^2$ and $R^3$ and $R^4$ in A are as hereinbefore defined ($R^3$ and $R^4$ being optionally protected if appropriate); $R^6$ and $R^7$ are hydrogen or carboxy protecting groups; $R^8$ is hydrogen or an amino protecting group; $R^9$ is hydrogen or an amino protecting group; and $R^{10}$ is a group $R^1$, protected 1-hydroxyethyl or protected hydroxymethyl; and wherein at least one protecting group is present; and thereinafter if necessary;

(i) forming a pharmaceutically acceptable salt, (ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12 C)alkyl groups (e.g. isopropyl, t-butyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); diaryl(lower alkyl)silyl groups (e.g. t-butyldiphenylsilyl); and (2–6 C)alkenyl groups (e.g. allyl and vinylethyl).

Methods particularly appropriate for the removal of carboxyl protecting groups include for example acid-, base-, metal- or enzymically-catalysed hydrolysis, for groups such as p-nitrobenzyloxy carbonyl, hydrogenation, and for groups such as o-nitrobenzyloxycarbonyl, photolyric methods.

Examples of hydroxyl protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl) groups; diaryl (lower alkyl)silyl groups (e.g. t-butyldiphenylsilyl); and aryl lower alkyl (e.g. benzyl) groups.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl); trialkylsilyl (e.g. trimethylsilyl and t-butyldimethylsilyl) groups; diaryl (lower alkyl) silyl groups (e.g. t-butyldiphenylsilyl); alkylidene (e.g. methylidene); benzylidene and substituted benzylidene groups.

Methods appropriate for the removal of hydroxy and amino protecting groups include for example acid-, base-, metal- or enzymically-catalysed hydrolysis, for groups such as p-nitrobenzyloxy carbonyl, hydrogenation, and for groups such as o-nitrobenzyloxycarbonyl, photolytic methods.

In another aspect of the present invention the compounds of the formulae (I) and (V) may be prepared by
a) reacting compounds of the formulae (VI) and (VII):

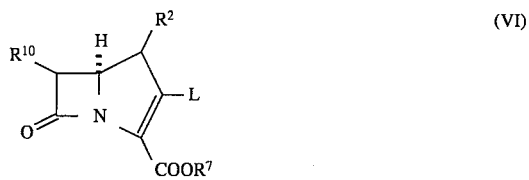

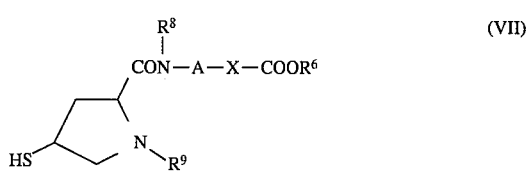

wherein A, X, $R^2$–$R^{10}$ are as hereinbefore defined and L is a leaving group, or
b) cyclising a compound of the formula (VIII):

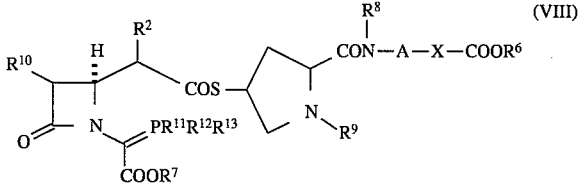

wherein A, X, $R^2$–$R^{10}$ as hereinbefore defined and $R^{11}$–$R^{13}$ are independently selected from $C_{1-6}$alkoxy, aryloxy, di-$C_{1-6}$alkylamino and diarylamino or any two of $R^{11}$–$R^{13}$ represent o-phenylenedioxy; or one of $R^{11}$–$R^{13}$ is $C_{1-4}$alkyl, allyl, benzyl or phenyl, and the other two values are independently selected from $C_{1-4}$alkyl, trifluoromethyl or phenyl, wherein any phenyl group is optionally substituted with $C_{1-3}$alkyl or $C_{1-3}$alkoxy:
and wherein any functional group is optionally protected and thereinafter if necessary:

(i) removing any protecting groups;

(ii) forming a pharmaceutically acceptable salt;

(iii) esterifying to form an in vivo hydrolysable ester.

Suitably in the compound of the formula (VI) L is the reactive ester of a hydroxy group such as a sulphonate (for example $C_{1-6}$alkanesulphonyloxy, trifluoromethanesulphonyloxy, benzenesulphonyloxy, toluenesulphonyloxy), a phosphoric ester (for example a diarylphosphoric ester such as diphenylphosphoric ester) or L is a halide (for example chloride). In an alternative L is a sulphoxide for example —SOCH=CH—NHCOCH3 which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient, suitably at about −20° C. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

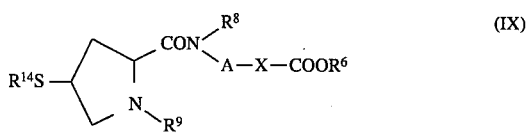
(IX)

wherein A, X, $R^3$–$R^6$, $R^8$ and $R^9$ as hereinbefore defined and $R^{14}$ is a protecting group, for example $C_{1-6}$alkanoyl or $C_{1-6}$alkoxycarbonyl. Preferred values for $R^{14}$ are acetyl and t-butoxycarbonyl. The compounds of the formula (IX) can be converted to the compounds of the formula (VII) by standard methods of deprotection, for example acetyl groups can be removed by basic hydrolysis in aqueous alkanol or alkenol for example allyl alcohol.

The compounds of the formula (IX) are novel and form another aspect of the present invention.

The compounds of the formula (IX) may be prepared by the reaction of an activated derivative of a compound of the formula (X), which may be formed in situ, with a compound of the formula (XI):

(X)

$R^8NH-A-X-COOR^6$ (XI)

wherein A, X, $R^3$–$R^6$, $R^8$, $R^9$ and $R^{14}$ are as hereinbefore defined. Activated derivatives of the compound of the formula (X) include acid halides, anhydrides and 'activated' esters such as 1H-benzo[1,2,3]triazol-1-yl, pentafluorophenyl and 2,4,5-trichlorophenyl esters or the benzimidazol-2-yl ester of the thiocarboxylic acid corresponding to (X). The reaction of the compounds of the formulae (X) and (XI) is performed under standard methods, for example in the presence of Vilsmeier reagent (thus forming the reactive derivative of (X) in situ) at temperatures in the region −30° C. to 25° C., preferably in the region −20° C. to 5° C., or in the presence of sulphonyl chloride at ambient temperature.

The compounds of the formulae (X) and (XI) are prepared by standard methods known to the skilled chemist such as the methods of the Examples hereinafter, the methods described in EP-A-126587 or by methods analogous or similar thereto.

Compounds of the formula (IX), wherein X contains a —$CONR^3$—group directly linked to ring A, may also be prepared by reacting activated derivative of a compound of the formula (XX), which may be formed in situ, with a compound of formula (XXI):

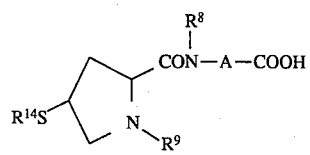
(XX)

$HN(R^5)-X^1-COOR^6$ (XXI)

wherein $R^5$, $R^6$, $R^8$, $R^9$ and $R^{14}$ are as hereinbefore defined and $X^1$ is alkanediyl. Activated derivatives of the compounds of formula (XX) may include the activated derivatives described for the compounds of formula (X).

In general, the reaction between compounds of the formulae (XX) and (XXI) is performed under similar conditions to those used in the reaction between compounds of the formulae (X) and (XI). The reaction may be performed between the acid chloride of (XX) and a compound of formula (XXI) in a solvent such as dichloromethane in the presence of trimethylsilylchloride and a base such as diisopropylethylamine in a temperature range of −30° C. to 25° C.

The compounds of the formula (XX) may be prepared by reacting a compound of the formula (X) with a compound of the formula $R^8NH-A-COOR^{20}$, wherein $R^{20}$ is a carboxy protecting group, and subsequently removing $R^{20}$. The compounds of the formulae (XX) and $R^8NH-A-COOR^{20}$ may be reacted together under similar conditions to those described for the reaction between compounds of the formulae (X) and (XI).

The compounds of the formulae (XXI) and $R^8NH-A-COOR^{20}$ are either known in the art or prepared by standard methods known to the skilled chemist.

Suitably, in the compounds of the formula (VIII), $R^{11}$–$R^{13}$ are independently selected from $C_{1-6}$ alkoxy such as methoxy, ethoxy, isopropoxy, n-propoxy or n-butoxy; aryloxy such as optionally phenoxy; di-$C_{1-6}$alkylamino such as dimethylamino or diethylamino; diarylamino such as diphenylamino or any two of $R^{11}$–$R^{13}$ represent o-phenylenedioxy. Preferably each of $R^{11}$–$R^{13}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

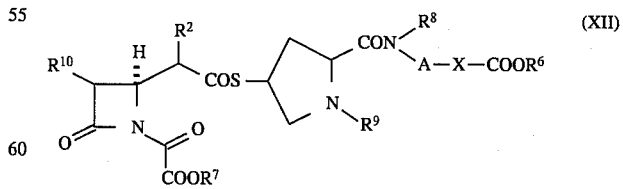
(XII)

$PR^{11}R^{12}R^{13}$ (XIII)

wherein A, X, $R^2$–$R^{13}$ are as hereinbefore defined.

Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

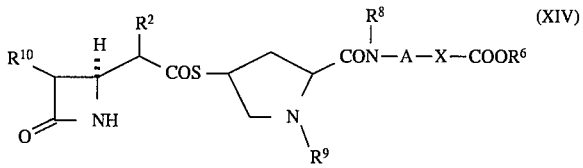

wherein A, X, $R^2$–$R^6$, and $R^8$–$R^{10}$ are as hereinbefore defined with a compound of the formula (XV):

$$Cl-CO-COOR^7 \qquad (XV)$$

wherein $R^7$ is as hereinbefore defined.

The compounds of the formula (XIV) may be prepared by reacting compounds of the formulae (XVI) and (VII):

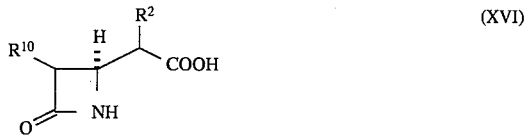

wherein $R^2$ and $R^{10}$ are as hereinbefore defined. The compounds of the formula (XVI) are known in the art and may be reacted with the compounds of the formula (VII) under conventional acylation methods known in the art.

Compounds of the formulae (V), (VII), (VIII), (IX), (XII) and (XIV) are novel and, as such, form another aspect of this invention.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and in general show particularly good pharmacokinetics especially with regard to half life in mammals. Representative compounds show significant improvement over imipenem.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to marmosets at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| | MIC (µg/ml) | | | | |
|---|---|---|---|---|---|
| | EXAMPLE | | | | |
| ORGANISM | 1 | 2 | 3 | 7 | ceftriaxone |
| Enterobacter cloacae -029 | 0.13 | 0.25 | 0.06 | 0.13 | 0.06 |
| E. coli TEM | 0.03 | 0.06 | 0.03 | 0.03 | 0.03 |
| S. aureus 147N | 0.13 | 0.25 | 0.25 | 0.25 | 2.0 |
| Enterobacter cloacae 108 | 2.0 | 4.0 | 1.0 | 1.0 | 32.0 |

In the examples:
(a) NMR spectra were taken at 200 MHz, 250 MHz or 400 MHz;
(b) Allyloxy means the propen-1-yloxy group $-OCH_2CH=CH_2$ and allyl means the propen-1-yl group $-CH_2CH=CH_2$;
(c) THF means tetrahydrofuran;
(d) DMF means dimethylformamide;
(e) Meldrum's acid is 2,2-dimethyl-1,3-dioxane-4,6-dione.
(f) Evaporation of solvents was carried out under reduced pressure.

POSITION OF PHENYL SUBSTITUENTS

| Example | 2 | 3 | 4 | 5 | 6 |
|---|---|---|---|---|---|
| 1 | H | E—CH=CHCOOH | H | H | H |
| 2 | H | E—CH=CHCOOH | H | H | OH |
| 3 | H | OCH$_2$COOH | H | H | H |
| 4 | H | CH$_2$CH$_2$COOH | H | H | H |
| 5 | H | CH$_2$COOH | H | H | OH |
| 6 | H | CH$_2$COOH | H | H | H |
| 7 | H | CONHCH$_2$COOH | H | H | H |
| 8 | H | CH$_2$OCH$_2$COOH | H | H | H |
| 9 | H | SCH$_2$COOH | H | H | H |

EXAMPLE 1

(1R,5S,6S,8R,2'S, 4'S)-2-(2-(3-(E- 2-carboxy-1-ethenyl)phenylcarbamoyl)-pyrrolidin- 4-ylthio)-6-(1-hydroxyethyl)-1-methylcarbapenem-3-carboxylic acid, disodium salt To a solution of allyl (1R,5S,6S,8R,2'S,4'S)-2-(1-allyloxycarbonyl- 2-(3-(E-2-allyloxycarbonyl-1-ethenyl)phenylcarbamoyl)-pyrrolidin- 4-ylthio)-6-(1-hydroxyethyl)-1-methylcarbapenem-3-carboxylate (240 mg, 0.36 mM) and Meldrum's acid (312 mg, 2.16 mM) in a mixture of DMF (2 ml) and THF (1 ml), under an argon atmosphere was added tetrakis(triphenylphosphine)palladium (42 mg, 0.036 mM). The solution was stirred, under argon with protection from the light, for 1 hour. A solution of sodium 2-ethylhexanoate (120 mg, 0.72 mM) in THF (2 ml) was added, followed by THF (10 ml). The precipitated product was separated by centrifugation, and washed successively with small portions of THF and diethyl ether, and dried. Crude material was dissolved in water (10 ml) and NaHCO$_3$ (120 mg) added with stirring, and the mixture purified by chromatography on a CHP2OP column eluted with water, to give title compound (26%).

NMR (DMSO-d$_6$/CD$_3$COOD): δ1.19 (d, 6H); 1.79 (m, part obscured, 1H); 2.63–2.78 (m, 1H); 2.88 (dd, 1H); 3.21 (dd, 1H); 3.40 (m, 1H); 3.49 (dd, 1H); 3.73 (quintet, 1H); 3.99 (quintet, 1H); 4.05 (t, 1H); 4.18 (dd, 1H); 6.48 (d, 1H); 7.39 (m, 2H); 7.55 (d, 1H); 7.73 (m, 1H); 7.91 (d, 1H).

MS (+ve FAB): 524 (MH)$^+$ (mono Na salt); 546 (MH)$^+$ (di Na salt).

The starting materials were prepared as follows:

Allyl 3-nitrocinnamate

3-Nitrocinnamic acid (5.0, 25.9 mM) was dissolved in DMF (50 ml), and anhydrous K$_2$CO$_3$ (7.15 g, 51.8 mM) added with stirring. Allyl bromide (3.36 ml, 38.8 mM) was run in, and the mixture stirred for 18 hours at ambient temperature. After filtration, the solvent was evaporated, the residue treated with water, and product extracted into diethyl ether (2 ×100 ml). The organic solution was washed with an aqueous solution of NaHCO$_3$, water, and brine, and dried (MgSO$_4$). Evaporation of the solvent gave title compound (6 g).

NMR (CDCl$_3$): δ4.74 (dt, 2H); 5.29–5.45 (m, 2H); 5.94–6.09 (m, 1H); 6.59 (d, 1H); 7.59 (t, 1H); 7.75 (d, 1H); 7.83 (dm, 1H); 8.24 (dm, 1H); 8.40 (t, 1n).

MS (CI): 233 H$^+$; 251 (M+NH$_4$)$^+$.

Allyl 3-aminocinnamate

Crude allyl 3-nitrocinnamate (3 g, 12.9 mM) was dissolved in ethyl acetate (10 ml) and added slowly to a stirred suspension of SnCl$_2$.2H$_2$O(14.52 g, 64 mM) in ethyl acetate (20 ml). The mixture was refluxed under argon for 3 hours, cooled, and poured into a mixture of ammonia (sg 880, 15 ml) and water (5 ml). Ethyl acetate (50 ml) was added, and the organic layer separated by decantation. Two further extractions with ethyl acetate (each 50 ml) were made similarly. The combined extracts were washed with water and brine, dried (MgSO$_4$) and evaporated to give title compound (2.6 g).

NMR (CDCl$_3$): δ3.55 (br, 2H); 4.70 (dt, 2H); 5.23–5.42 (m, 2H); 5.89–6.09 (m, 1H); 6.40 (d, 1H); 6.72 (dm, 1H); 6.83 (t, 1H); 6.93 (dm, 1H); 7.17 (t, 1H); 7.62 (d, 1H).

MS (CI): 204 (MH)$^+$; 221 (H+NH$_4$)$^+$.

(2S,4S)-4-Acetylthio-1-allyloxycarbonyl-2-(3,(E-2-allyloxycarbonyl- 1ethenyl)phenylcarbamoyl)pyrrolidine Vilsmeier reagent was prepared by treatment of DMF (0.63 ml, 8.1 mM) in dichloromethane (25 ml) under argon with oxalyl chloride (0.64 ml, 7.4 mM) at −10° for 30 minutes. (2S,4S)- 4-Acetylthio-1-allyloxycarbonyl-2-carboxypyrrolidine (2.02 g, 7.4 mM) in dichloromethane (5 ml) was added to this in one portion, followed by N-methylmorpholine (0.97 ml, 8.9 mM) in dichloromethane (3 ml) and stirring continued for 30 minutes at −15°. After cooling to −20°, allyl 3-aminocinnamate (1.5 g, 7.4 mM) and N-methylmorpholine (0.97 ml, 8.9 mM) in dichloromethane (5 ml) were added. The temperature was allowed to rise to 5° and stirring continued for 18 hours. After dilution with dichloromethane (100 ml), the mixture was washed with 1M hydrochloric acid (20 ml), water, saturated aqueous NaHCO$_3$, and brine, and dried (MgSO$_4$). Purification by medium pressure chromatography using a gradient of dichloromethane to dichloromethane/diethyl ether (9:1) gave title compound (1.39 g).

NMR (CDCl$_3$): Δ2.32 (s, 3H); 2.50 (br m, 2H); 3.39 (dd, 1H); 4.03 (quintet, 1H); 4.15 (dd, 1H); 4.56 (t, 1H); 4.63–4.73 (m, 4H); 5.22–5.43 (m, 4H); 5.85–6.09 (m, 2H); 6.47 (d, 1H); 7.26 (dm, 1H); 7.32 (t, 1H); 7.50 (dt, 1H); 7.67 (d, 1H); 7.77 (br s, 1H); 9.72 (br, 1H). MS (CI): 459 (MH)$^+$.

(2S, 4S)-1-Allyloxycarbonyl-2-(3-(E-2-allyloxycarbonyl-1-ethenyl)phenyl-carbamoyl)pyrrolidin-4-ylthiol (2S,4S)-4-Acetylthio-1-allyloxycarbonyl-2-(3-(E- 2-allyloxycarbonyl-1-ethenyl)phenylcarbamoyl)pyrrolidine (1.3 g, 2.84 mM) was dissolved in allyl alcohol (30 ml), and the solution flushed with argon. A 1M aqueous solution of sodium hydroxide (3.0 ml, 3 mM) was added and the mixture was stirred at ambient temperature for 3 hours. Glacial acetic acid (0.25 ml) was added, and solvent removed by evaporation. The residue taken up in ethyl acetate (50 ml), and washed with 2M hydrochloric acid (10 ml), followed by water (10 ml), aqueous NaHCO$_3$ (10 ml), and brine, and dried (MgSO$_4$). Removal of the solvent gave title compound (1.15 g). This was used immediately in the next stage.

Allyl (1R,5S,6S,8R,2'S,4'S)-2-(1-allyloxycarbonyl- 2-(3-(E- 2-allyloxy-carbonyl- 1ethenyl-)phenylcarbamoyl)pyrrolidin-4-ylthio)-6-(1-hydroxy-ethyl)- 1-methylcarbapenem-3-carboxylate A solution of allyl (1R,5R,6S,8R)-6-(1-hydroxyethyl)-1-methyl-2-diphenylphosphoryloxycarbapenem-3-carboxylate (1.24 g, 2.49 mM) was dissolved in dry acetonitrile (15 ml) at −20°, and the flask flushed with argon. Ethyldiisopropylamine (0.48 ml, 2.74 mM) was added, followed by (2S,4S)-1-allyloxycarbonyl-2-(3-(E- 2-allyloxycarbonyl-1-ethenyl)carbamoyl)pyrrolidin-4-ylthiol (1.14 g, 2.74 mM) in acetonitrile (5 ml), and the mix stored at −20° for 24 hours. The solvent was evaporated and the residue purified by medium pressure chromatography with gradient elution from dichloromethane to dichloromethane/ethyl acetate (1:1) to give title compound (500 mg).

NMR (CDCl$_3$): δ1.26 (d, 3H); 1.34 (d, 3H); 2.65 (br m, 2H); 3.26,3.30 (dd overlapping quintet, 2H); 3.50 (br m, 1H); 3.80 (quintet, 1H); 3.99 (dd, 1H) 4.20–4.31 (overlapping m, 2H); 4.54 (t, 1H); 4.63–4.76 (m, 6H); 5.19–5.44 (m, 6H); 5.85–6.08 (m, 3H); 6.51 (d, 1H); 7.24 (m, 1H) 7.37 (t, 1H); 7.59 (d, 1H); 7.70 (d, 1H); 7.81 (br s, 1H); 8.93 (br, 1H).

MS (+ve FAB): 666 (MH)$^+$; 688 (M+Na)$^+$.

EXAMPLE 2

1R,5S,6S,8R,2'S,4'S)-2-(2-(3-(E- 2-Carboxy-1-ethenyl)-6-hydroxyphenyl-carbamoyl)pyrrolidin- 4-ylthio)-6-(1-hydroxyethyl)-1-methylcarbapenem-3carboxylic acid, disodium salt The title compound was prepared from the corresponding allyl protected compound by the method described in example 1, except that the crude sodium salt was precipitated by ether, not THF.

NMR (DMSO-d$_6$/CD$_3$COOD): δ1.18 (d, 6H); 1.78 (m, 1H); 2.60–2.86 (m, 2H); 3.20 (dd, 1H); 3.41 (quintet, 1H); 3.47–3.69 (m, 2H); 3.93–4.08 (m, 2H); 4.07 (dd, 1H); 6.23 (d, 1H); 6.93 (d, 1H); 7.24 (dd, 1H); 7.49 (d, 1H); 8.44 (d, 1H).

MS (−ve FAB): 516 (M−H)$^-$.

The starting materials were prepared as follows:

4-Hydroxy-3-nitrobenzaldehyde was allylated using the method described in example 1, using 4-hydroxy-3-nitrobenzaldehyde in place of 3-nitrocinnamic acid to give 4-allyloxy-3-nitrobenzaldehyde. NMR (CDCl$_3$): δ4.80 (dr, 2H); 5.36–5.56 (m, 2H); 5.96–6.16 (m, 1H); 7.22 (d, 1H); 8.06 (dd, 1H) 8.35 (d, 1H) 9.34 (s, 1H).

MS (+ve FAB): 207 (MH)$^+$.

4-Allyloxy-3-nitrocinnamic acid

4-Allyloxy-3-nitrobenzaldehyde (5 g, 24.1 mM) was dissolved in pyridine (100 ml) and malonic acid (5.02 g, 48.3 mM) and piperidine (0.48 ml, 4.8 mM) added. The mixture was heated to reflux with stirring for 2 hours, cooled, and poured onto a mixture of concentrated hydrochloric acid and ice. Organics were extracted into ethyl acetate, the organic layer washed with 2M hydrochloric acid, and product back-extracted into aqueous NaHCO$_3$. The aqueous solution was then re-acidified (concentrated hydrochloric acid), and organics extracted into ethyl acetate, washed with brine, and dried (MgSO4), to give title compound (4.23 g).

NMR (CDCl$_3$): δ4.74 (dt, 2H); 5.33–5.56 (m, 2H); 5.95–6.05 (m, 1H); 6.40 (d, 1H); 7.11 (d, 1H); 7.68,7.69 (dd overlapping d, 2H) 8.03 (d, 1H).

MS (EI): 249 H$^+$.

4-Allyloxy-3-nitrocinnamic acid was allylated using the method described in example 1, using 4-allyloxy-3-nitrocinnamic acid in place of 3-nitrocinnamic acid to give allyl 4-allyloxy-3-nitrocinnamate.

NMR (CDCl$_3$): δ4.72 (m, 4H); 5.25–5.53 (m, 4H); 5.91–6.11 (m, 2H); 6.41 (d, 1H); 7.09 (d, 1H); 7.63 (d, 1H); 7.65 (dd, 1H) 8.01 (d, 1H).

MS (EI): 189 M$^+$.

Allyl 4-allyloxy-3-nitrocinnamate was reduced by the method described in example 1 using allyl 4-allyloxy-3-nitrocinnamate in place of allyl 3-nitrocinnamate, to give allyl 4-allyloxy-3-aminocinnamate.

NMR (CDCl$_3$): δ3.75 (br, 2H); 4.60 (dt, 2H); 4.70 (dt, 2H); 5.22–5.45 (m, 4H); 5.89–6.16 (m, 2H); 6.27 (d, 1H); 6.76 (d, 1H); 6.86–6.91 (m, 2H); 7.59 (d, 1H).

MS (CI): 260 (MH)$^+$.

Allyl 4-allyloxy-3-aminocinnamate was condensed with (2S,4S)-4-acetylthio-1-allyloxycarbonyl-2-carboxypyrrolidine by the method described in example 1 for allyl 3-aminocinnamate to give (2S,4S)-4-acetylthio-1-allyloxycarbonyl-2-(6-allyloxy-3-(E-2-allyloxycarbonyl-1-ethenyl)phenylcarbamoyl)pyrrolidine.

NMR (CDCl$_3$): δ2.31 (s, 3H); 2.49 (br, 1H); 2.68 (br, 1H); 3.40 (dd, 1H); 4.03 (quintet, 1H); 4.16 (dd, 1H); 4.57 (m, part obscured, 1H); 4.60–4.72 (m, 6H); 5.18–5.47 (m, 6H); 5.81–6.17 (m, 3H); 6.41 (d, 1H); 6.87 (d, 1H); 7.20 (dd, 1H); 7.66 (d, 1H); 8.67 (d, 1H); 8.97 (br, 1H). MS (−ve FAB): 513 (M−H)$^−$.

(2S,4S)-4-Acetylthio-1-allyloxycarbonyl-2-(6-allyloxy-3-(E-2-allyloxycarbonyl-1-ethenyl)phenylcarbamoyl)pyrrolidine was deacetylated and condensed with allyl (1R,5R,6S,8R)-6-(1-hydroxyethyl)- 1-methyl-2-diphenylphosphoryloxycarbapenem-3-carboxylate by the method described in example 1 for (2S,4S)-4-acetylthio-1-allyloxycarbonyl-2-(3-(E-2-allyloxycarbonyl-1-ethenyl)phenylcarbamoyl)pyrrolidine, except that purification by medium pressure chromatography used a gradient elution from dichloromethane to ethyl acetate/dichloromethane (4:1), to give allyl (1R,5S,6S,8R,2'S,4'S)-2-(1-allyloxycarbonyl-2-(6-allyloxy-3-(E-2-allyloxycarbonyl-1-ethenyl)phenylcarbamoyl)pyrrolidin-4-ylthio)-6-(1-hydroxyethyl)-1-methylcarbapenem-3-carboxylate.

NMR (CDCl$_3$): δ1.27 (d, 3H); 1.35 (d, 3H); 2.47 (br, 1H); 2.68 (br, 1H); 3.25,3.29 (dd overlapping quintet, 2H); 3.44 (dd, 1H); 3.80 (quintet, 1H); 4.10–4.32 (m, 3H); 4.49–4.70 (complex m, 9H); 5.18–5.47 (m, 8H); 5.81–6.12 (m, 4H); 6.40 (d, 1H); 6.86 (d, 1H); 7.20 (dd, 1H); 7.65 (d, 1H); 8.67 (d, 1H); 8.84 (br, 1H).

MS (+ve FAB): 722 (MH)$^+$.

EXAMPLE 3

(1R,5S,6S,8R,2'S,4'S)-2-(2-(3-Carboxymethoxyphenylcarbamoyl)pyrrolidin-4-ylthio)-6-(1-hydroxyethyl)-1-methylcarbapenem-3-carboxylic acid, disodium salt The title compound was prepared from the corresponding allyl protected compound by the method described in example 1.

NMR (DMSO-d$_6$/CD$_3$COOD): δ1.19 (d, 6H); 1.94 (m, part obscured, 1H); 2.87 (m, 1H); 3.14 (dd, 1H); 3.24 (dd, 1H); 3.40 (quintet, 1H); 3.69 (dd, 1H); 3.92 (quintet, 1H); 4.02 (quintet, 1H); 4.21 (dd, 1H); 4.32 (t, 1H); 4.59 (s, 2H); 6.67 (dm, 1H); 7.17–7.30 (m, 3H).

MS (+ve FAB): 528 (MH)$^+$ (mono Na salt); 550 (MH)$^+$ (di Na salt).

The starting materials were prepared as follows:

3-Nitrophenoxyacetic acid was allylated using the method described in example 1, using 3-nitrophenoxyacetic acid in place of 3-nitrocinnamic acid to give allyl 3-nitrophenoxyacetate.

NMR (CDCl$_3$): δ4.72,4.74 (s, overlapping dt, 4H); 5.26–5.42 (m, 2H); 5.84–6.03 (m, 1H); 7.28 (dm, 1H); 7.46 (t, 1H); 7.73 (t, 1H); 7.89 (dm, 1H).

MS (EI): 237 M$^+$.

Allyl 3-aminophenoxyacetate

Allyl 3-nitrophenoxyacetate (5 g, 0.021M) was dissolved in a mixture of ethyl acetate (45 ml) and t-butanol (5 ml), and SnCl$_2$.2H$_2$O (23.79 g, 0.105M) added. After stirring and heating at 60° for 1 hour, sodium borohydride (399 mg, 0.0105M) was added in portions, and heating continued for another 2 hours. Solvent was removed, the residue was taken up in water, and the pH adjusted to 7.6 with aqueous NaHCO$_3$. Organics were extracted into ethyl acetate, and the combined organic layers washed with aqueous NaHCO$_3$, water, brine, and dried (MgSO$_4$). Evaporation gave the title compound (2.61 g).

NMR (CDCl$_3$): δ3.67 (br, 2H); 4.59 (s, 2H); 4.68 (din, 2H); 5.21–5.36 (m, 2H); 5.83–6.02 (m, 1H); 6.25–6.34 (m, 1H); 7.03 (t, 1H).

MS (CI): 207 (MH)$^+$.

(2S,4S)-4-Acetylthio-1-allyloxycarbonyl- 2-(3-allyloxycarbonylmethoxyphenylcarbamoyl)pyrrolidine (2S,4S)-4-Acetylthio-1-allyloxycarbonyl-2-carboxypyrrolidine (1.59 g, 5.82 mM), allyl 3-aminophenoxyacetate (2.5 g, 0.012M), and 2-ethoxy-1-ethoxycarbonyl-1,2-dihydroquinoline (3.88 g, 0.016M) were dissolved in toluene (50 ml) and stirred 18 h at ambient temperature. The reaction mixture was diluted with ethyl acetate (150 ml) and washed with 2M hydrochloric acid (2×30 ml), water, saturated NaHCO$_3$, and brine. Crude product was purified by chromatography on silica, using a gradient from dichloromethane to dichloromethane/diethyl ether (4:1), to give title compound (3.0 g).

NMR (CDCl$_3$): δ2.33 (s, 3H); 2.59 (br, 2H); 3.38 (br m, 1H); 4.02 (quintet, 1H); 4.13 (dd, 1H); 4.55 (t, 1H); 4.66, 4.63–4.75 (s overlapping m, 6H); 5.23–5.41 (m, 4H); 5.84–6.05 (m, 2H); 6.68 (dd, 1H); 7.05 (d, 1H); 7.22 (t, 1H); 7.32 (t, 1H); 9.14 (br, 1H).

MS (+ve FAB): 463 (MH)$^+$; 485 (M+Na)$^+$.

(2S,4S)-4-Acetylthio-1-allyloxycarbonyl-2-(3-allyloxycarbonylmethoxyphenylcarbamoyl)pyrrolidine was deacetylated and condensed with allyl (1R,5R,6S,8R)-6-(1-hydroxyethyl)-1-methyl-2-diphenylphosphoryloxycarbapenem-3-carboxylate by the method described in example 1 for (2S,4S)-4-acetylthio-1-allyloxycarbonyl-2-(3-(E-2-carboxy-1-ethenyl)phenylcarbamoyl)pyrrolidine, except that purification by medium pressure chromatography used a gradient elution from dichloromethane to ethyl acetate/dichloromethane (3:2), to give allyl (1R,5S,6S,8R,2'S,4'S)-2-(1-allyloxycarbonyl-2-( 3-allyloxy-carbonylmethoxyphenylcarbamoyl)pyrrolidin- 4-ylthio)-6-(1-hydroxyethyl)1-methylcarbapenem-3-carboxylate.

NMR (CDCl$_3$): δ1.24 (d, 3H); 1.36 (d, 3H); 2.64 (br, 2H); 3.26 (dd overlapping m, 2H); 3.48 (br, 1H); 3.80 (quintet, 1H); 4.02 (dd, 1H); 4.44 (dd overlapping m, 2H); 4.51 (t, 1H); 4.70,4.65–4.75 (s overlapping m, 8H); 5.21–5.47 (m, 6H); 5.87–6.02 (m, 3H); 6.70 (dm, 1H); 7.09 (br d, 1H); 7.23 (t, 1H); 7.35 (t, 1H); 8.87 (br, 1H).

MS (+ve FAB): 670 (MH)$^+$; 692 (M+Na)$^+$.

EXAMPLE 4

(1R,5S,6S,8R,2'S,4'S)-2-(2-(3-( 2-Carboxyethyl)phenylcarbamoyl)-pyrrolidin- 4-ylthio)-6(1-hydroxyethyl)-1-methylcarbapenem-3-carboxylic acid, disodium salt The title compound was prepared from the corresponding allyl protected compound by the method described in example 1.

NMR (DMSO-d$_6$/CD$_3$COOD): δ1.20 (d, 6H); 1.96 (m, part obscured, 1H); 2.56 (t, part obscured, 2H); 2.86,2.92 (t overlapping m, 3H); 3.17–3.29 (overlapping m, 2H); 3.41 (quintet, 1H); 3.75 (dd, 1H); 3.96 (quintet, 1H); 4.03 (quintet, 1H); 4.22 (dd, 1H); 4.39 (t, 1H); 7.01 (d, 1H); 7.26 (t, 1H); 7.49 (m, 2H).

MS (+ve FAB): 526 (MH)$^+$ (mono Na salt); 548 (MH)$^+$ (di Na salt).

The starting materials were prepared as follows:
3-(3-Aminophenyl)propionic acid 3-Nitrocinnamic acid (1.5 g, 7.77 mM) was suspended in a mixture of ethanol (80 ml) and water (20 ml), and palladium on charcoal (10%, 100 mg) added. The mixture was shaken in an atmosphere of hydrogen for 4.5 hours, when uptake of gas complete. After filtration through diatomaceous earth, the solvent was removed to give title compound.

NMR (CDCl$_3$): δ2.65 (t, 2H); 2.87 (t, 2H); 4.44 (br, 2H); 6.52–6.63 (m, 3H); 7.08 (t, 1H).

MS (CI): 166 (MH)$^+$.
Allyl 3-(3-Aminophenyl)propionate 3-(3-Aminophenyl)propionic acid (1 g, 6.06 mM) was dissolved in allyl alcohol (25 ml), and toluene-4-sulfonic acid (1.21 g, 6.36 mM) added. The mixture was heated to reflux, the distillate being passed through 3 Å molecular sieves, for 24 hours. After neutralisation of the mixture with triethylamine, the solvent was removed, the residue dissolved in ethyl acetate, and washed with water, aqueous NaHCO$_3$, brine, and dried (MgSO$_4$), to give title compound.

NMR (CDCl$_3$): δ2.63 (t, 2H); 2.87 (t, 2H); 3.61 (br, 2H); 4.58 (dr, 2H); 5.18–5.34 (m, 2H); 5.81–6.00 (m, 1H); 6.51–6.61 (m, 3H); 7.06 (t 1H).

MS (CI): 206 (MH)+; 223 (M+NH$_4$)$^+$.

Allyl 3-(3-aminophenyl)propionate was condensed with (2S,4S)-4-acetylthio-1-allyloxycarbonyl-2-carboxypyrrolidine by the method described in example 3 for allyl 3-nitrophenoxyacetate, except that crude product was purified by chromatography on silica, using a gradient from dichloromethane to dichloromethane/diethyl ether (1:1), to give (2S,4S)-4-acetylthio-1-allyloxycarbonyl-2-( 3-2-allyloxycarbonylethyl)phenylcarbamoyl)pyrrolidine.

NMR (CDCl$_3$): δ2.33 (s, 3H); 2.65 (t, overlapping br m, 4H); 2.95 (t, 2H); 3.39 (dd, 1H); 4.03 (quintet, 1H); 4.13 (dd, 1H); 4.54 (t, part obscured, 1H); 4.57–4.70 (m, 4H); 5.21–5.38 (m, 4H); 5.83–6.01 (m, 2H); 6.86 (d, 1H); 7.23 (t, 1H); 7.33–7.42 (m, 2H); 8.99 (br, 1H). MS (+ve FAB): 461 (MH)$^+$; 483 (M+Na)$^+$.

(2S,4S)-4-Acetylthio-1-allyloxycarbonyl-2-(3(2-allyloxycarbonylethyl)phenylcarbamoyl)pyrrolidine was deacetylated and condensed with allyl (1R,5R,6S,8R)-6-(1-hydroxyethyl)-1-methyl- 2-diphenylphosphoryloxycarbapenem-3-carboxylate by the method described in example 1 for (2S,4S)-4-acetylthio-1-allyloxycarbonyl-2-(3-(E- 2-allyloxycarbonyl-1-ethenyl)phenylcarbamoyl)pyrrolidine, except that purification by medium pressure chromatography used a gradient elution from dichloromethane to ethyl acetate/dichloromethane (7:3), to give allyl (1R,5S,6S,8R, 2'S,4'S)-2-(1-allyloxycarbonyl-2(3-(2-allyloxycarbonylethyl)phenylcarbamoyl)pyrrolidin-4-ylthio)-6-(1-hydroxyethyl)- 1-methylcarbapenem-3-carboxylate.

NMR (CDCl$_3$): δ1.26 (d, 3H); 1.36 (d, 3H); 2.69 (t overlapping br m, 4H); 2.97 (t, 2H); 3.26,3.30 (dd overlapping quintet, 2H); 3.48 (br m, 1H); 3.80 (quintet, 1H); 4.02 (dd, 1H); 4.21-4.29 (m, 2H); 4.51 (t, 1H); 4.57–4.80 (m, 6H); 5.20–5.44 (m, 6H); 5.82–6.01 (m, 3H); 6.97 (d, 1H); 7.24 (t, 1H); 7.38–7.46 (m, 2H); 8.80 (br, 1H).

MS (+ve FAB): 668 (MH)$^+$; 690 (M+Na)$^+$.

EXAMPLE 5

(1R,5S,6S,8R,2'S 4'S)-2-(2-( 5-Carboxymethyl-2-hydroxyethylcarbamoyl)-pyrrolidin- 4-ylthio)-6-(1hydroxyethyl)-1-methylcarbapenem-3-carboxylic acid To a solution of allyl (1R,5S,6S,8R,2'S,4'S)-2-( 1-allyloxycarbonyl-2-(2-allyloxy-5-allyloxycarbonylmethylphenyl-carbamoyl)pyrrolidin- 4-ylthio)-6-(1-hydroxyethyl)-1-methylcarbapenem-3carboxylate (1.0 g, 1.55 mM) and Meldrum's acid (1.79 g, 12.4 mM) in a mixture of DMF (8 ml) and THF (4 ml), under an argon atmosphere was added tetrakis(triphenylphosphine)palladium (173 mg, 0.15 mM). The solution was stirred, under argon with protection from the light, for 1 hour, then dry THF (12 ml) was added, followed by anhydrous diethyl ether (50 ml). The precipitated product was separated by centrifugation, and washed successively with small portions of THF and diethyl ether, and dried. Crude material was dissolved in water and purified by chromatography on a CHP$_2$OP column eluted with water, to give title compound (12%).

NMR (DMSO-d6/CD$_3$COOD): δ1.18 (d, 6H); 1.81 (m, part obscured, 1H); 2.61–2.87 (overlapping m, 2H); 3.23 (dd, 1H); 3.44 (s, overlapping m, 3H); 3.60 (dd, 1H); 3.72 (quintet, 1H); 4.02 (quintet, 1H); 4.17 (t overlapping dd, 2H); 6.84 (br s, 2H); 7.97 (m, 1H).

MS (+ve FAB): 506 (MH)$^+$; 528 (M+Na)$^+$

The starting materials were prepared as follows:
  4-Hydroxy-3-nitrophenylacetic acid was allylated using the method described in example 1, using 4-hydroxy-3-nitrophenylacetic acid in place of 3-nitrocinnamic acid to give allyl 4-allyloxy-3-nitrophenylacetate.

NMR (CDCl$_3$): δ3.64 (s, 2H); 4.61 (dt, 2H); 4.68 (dt, 2H); 5.21–5.53 (m, 4H); 5.82–6.13 (m, 2H); 7.04 (d, 1H); 7.44 (dd, 1H); 7.79 (d, 1H).

Allyl 4-allyloxy-3-nitrocinnamate was reduced by the method described in example 1 using allyl 4-allyloxy-3-nitrophenylacetate in place of allyl 3-nitrocinnamate, to give allyl 4-allyloxy-3-aminophenylacetate.

NMR (CDCl$_3$): δ3.50,3.52 (s overlapping br, 4H); 4.53–4.60 (m, 4H); 5.18–5.43 (m, 4H); 5.83–6.14 (m, 2H); 6.60 (dd, 1H); 6.68 (d, 1H); 6.72 (d, 2H).

MS (CI): 248 (MH)$^+$.

Allyl 4-allyloxy-3-aminophenylacetate was condensed with (2S,4S)-4-acetylthio-1-allyloxycarbonyl-2-carboxypyrrolidine by the method described in example 1 for allyl 3-aminocinnamate to give, after purification by chromatography on silica, using a gradient from dichloromethane to dichloromethane/diethyl ether (9:1), (2S,4S)- 4-acetylthio- 1-allyloxycarbonyl-2-(2-allyloxy- 5-allyloxycarbonylmethylphenylcarbamoyl)pyrrolidine.

NMR (CDCl₃): δ2.30 (s, 3H); 2.47 (br, 1H); 2.68 (br, 1H); 3.40 (dd, 1H); 3.60 (s, 2H); 4.03 (quintet, 1H); 4.17 (dd, 1H); 4.54 (m, part obscured, 1H); 4.57–4.65 (m, 6H); 5.18–5.45 (m, 6H); 5.80-6.17 (m, 6.83 (d, 1H); 6.98 (dd, 1H); 8.32 (d, 1H); 8.90 (br, 1H).

MS (+ve FAB): 503 (MH)⁺; 525 (M+Na)⁺.

(2S,4S)-4-Acetylthio-1-allyloxycarbonyl-2-(2-allyloxy-5-allyloxycarbonylmethylphenylcarbamoyl)pyrrolidine was deacetylated and condensed with allyl (1R,5R,6S,8R)-6-(1-hydroxyethyl)-1-methyl-2-diphenylphosphoryloxycarbapenem-3-carboxylate by the method described in example 1 for (2S,4S)-4-acetylthio-1-allyloxycarbonyl-2(3-(E-2-allyloxycarbonyl-1-ethenyl)phenylcarbamoyl)pyrrolidine, except that purification by medium pressure chromatography used a gradient elution from dichloromethane to ethyl acetate, to give allyl (1R,5S,6S,8R,2'S,4'S)- 2-(1-allyloxycarbonyl-2-(2-allyloxy- 5-allyloxy-carbonylmethylphenylcarbamoyl)pyrrolidin- 4-ylthio)-6-(1-hydroxyethyl)1-methylcarbapenem-3-carboxylate.

NMR (CDCl₃): δ1.18 (d, 3H); 1.35 (d, 3H); 2.43 (br, 1H); 2.67 (br, 1H); 3.21,3.23 (dd overlapping quintet, 2H); 3.43 (dd, 1H); 3.60 (s, 2H); 3.83 (quintet, 1H); 4.10–4.25 (overlapping m, 3H); 4.50–4.66 (overlapping m, 9H); 5.19–5.43 (m, 8H); 5.80–6.14 (m, 4H); 6.82 (d, 1H); 6.95 (dd, 1H); 8.32 (d, 1H); 8.73 (br, 1H).

MS (+ve FAB): 710 (MH)⁺; 732 (M+Na)⁺.

EXAMPLE 6

(1R, 5S,6S,8R,2'S,4'S - 2-(2-(3-Carboxymethylphenylcarbamoyl-pyrrolidin- 4-ylthio)-6-(1-hydroxyethyl)-1-methylcarbapenem-3-carboxylic acid dipotassium salt.

A solution of 4-nitrobenzyl (1R,5S,6S,8R,2'S,4'S)-2-(1-( 4-nitrobenzyloxycarbonyl)-2-(3-carboxymethylphenylcarbamoyl)pyrrolidin-4-ylthio)-6-(1-hydroxyethyl)-1-methylcarbapenem-3-carboxylate (940 mg, 1.17 mM) in a 1:1 mixture of H₂O/ethyl acetate (10 ml) in the presence of KHCO₃ (235 mg, 2.3 mM) was hydrogenated at atmospheric pressure with Pd/C (10%, 940 mg) for 2 hours. The reaction mixture was filtered through diatomaceous earth which was washed with water. The aqueous phase was recovered and the product purified by preparative HPLC (C₁₈ Nucleosil; eluents: CH₃CN/H₂O). The fractions containing pure product were collected, concentrated and freeze dried to give product (100 mg, 16%).

NMR (DMSO-d₆/CD₃COOD) 1.18 (2d, 6H); 1,75 (m, 1H); 2.65 (m, 1H); 2.82 (m, 1H); 3.18 (dd, 1H); 3.35 (m, 2H), 3.52 (s, 2H); 3.7 (m, 1H); 3.98 (m, 2H); 4.12 (dd, 1H); 6.98 (d, 1H); 7.22 (t, 1H); 7.52 (d, 1H); 7.58 (s, 1H).

MS (+ve FAB): 566 (MH)⁺ 604 (M+K)⁺.

The starting material was prepared as follows:
2S,4S)-1-(4-Nitrobenzyloxycarbonyl)-2-(- 3-carboxymethylphenylcarbamoyl)pyrrolidin- 4-ylthioacetate.

(2S,4S)-1-(4-Nitrobenzyloxycarbonyl)-4-acetylthio-2carboxypyrrolidin (2.44 g; 6.6 mM) was dissolved in SOCl₂ (10 ml) in the presence of a drop of DMF and stirred at room temperature overnight. Thionyl chloride was evaporated, the residual oil was then dissolved in toluene, evaporated and dried. The acid chloride in solution in CH₂Cl₂ (5 ml) was added to a solution of 3-aminophenylacetic acid (1 g, 6.6 mM) in CH₂Cl₂ (5 ml) in the presence of diisopropylethylamine (2.3 ml, 13.2 mM) at 0° C. The mixture was stirred for 1 hour at room temperature, the solvent evaporated, and the residue purified by HP 20SS chromatography, eluent H₂O/0.01 AcOH—CH₃CN, to give title compound (1 g, 30%).

NMR (DHSO-d6): 2.0 (m, 1H); 2.35 (s, 3H); 2.8 (m, 1H); 3.25 (m, 1H); 3.5 (s, 2H); 3.95–4.2 (m, 2H); 4.4–4.5 (dt, 1H); 5.1–5.3 (m, 2H); 7.0 (d, 1H); 7.25 (m, 1H); 7.5 (m, 3H); 7.7 (d, 1H); 7.95 (d, 1H); 8.25 (d, 1H ).

4-Nitrobenzyl. 1R,5S,6S,8R,2'S,4'S)-2-(1-( 4-nitrobenzyloxycarbonyl)2-(3-carboxymethylphenylcarbamoyl)pyrrolidin- 4-ylthio)-6-(1-hydroxyethyl)- 1-methylcarbapenem-3-carboxylate (2S,4S)-1-(4-Nitrobenzyloxycarbonyl)-2-(3-carboxymethylphenyl carbamoyl)pyrrolidin-4-ylthioacetate (1 g, 2 mM) in dioxane (10 ml) was stirred at room temperature with an aqueous solution of NaOH 1N (4 ml, 4 mM) for 2.5 hours. The mixture was then acidified to pH3 with 2N/HCl, evaporated and dried. The crude thiol thus obtained was solubilized in DMF (8 ml) in the presence of 4-nitrobenzyl (1R,SR,6S,8R)-6-(1-hydroxyethyl)-1-methyl-2-diphenylphosphoryloxy carbapenem-3-carboxylate (1.17 g, 2 mM), diisopropylamine (1 ml, 6 mM), Bu₃P (0.5 ml, 2 mM) and H₂O (4 μl) and stirred at room temperature for 3 hours. The crude reaction mixture was purified by chromatography over HP 20SS (eluent CH₃CN-H₂O) to give after evaporation of the required fractions, title compound (940 mg, 50%).

NMR: (DHSO-d6) 1.75 (m, 1H); 2.05 (m, 1H); 2.8 (m, 1H); 3.3 (dd, 1H); 3.45 (s, 2H); 3.6 (m, 1H); 4.0 (m, 2H); 4.3 (m, 2H); 4.5 (dt, 1H); 5.0–5.45 (m, 4H); 7.0 (d, 1H), 7.25 (m, 1H); 7.5 (t, 3H); 7.7 (m, 3H); 7.9 (d, 1H); 8.2 (m, 3H).

EXAMPLE 7

(1R,5S,6S,8R,2(2-(3-Carboxymethylaminocarbonylphenylcarbamoyl)-pyrrolidin- 4-ylthio)-6-(1-hydroxyethyl)-1-methylcarbapenem- 3-carboxylic acid, disodium salt.

To a solution of 4-nitrobenzyl (1R,5S,6S,8R,2'S,4'S)-2-(2-( 3-allyloxycarbonylmethylaminocarbonylphenylcarbamoyl)- 1-(4-nitrobenzyl-oxycarbonyl)pyrrolidin- 4-ylthio)-6-(1-hydroxyethyl)-1-methylcarbapenem3-carboxylate (270 mg, 0.28 mM) and Heldrum's acid (119 mg, 0.83 mM) in THF (4 ml), under an argon atmosphere with protection from the light, was added tetrakis(triphenylphosphine)palladium (32 mg, 0.028 mM). The mixture was stirred at ambient temperature for 20 minutes. The solution was added to a mixture of ethyl acetate (15 ml), water (15 ml) and NaHCO₃ (23 mg, 0.28 mM)o 10% Pd/charcoal (150 mg) was added and the mixture hydrogenated in an atmosphere of hydrogen for 3 hours. The catalyst was filtered, the filtrate was extracted with ethyl acetate (~20 ml) and ether (~20 ml) the pH adjusted from 4.5 to 7.0 with the addition of dilute aqueous NaHCO₃ solution and the aqueous layer was freeze-dried to give the title product (220 mg).

NMR δ: 1.31 (d,3H); 1.33 (d, 3H); 2.05–2.15 (m, 1H); 3.00–3.08 (m, 1H); 3.30–3.45 (m, 2H); 3.52 (quintet 1H); 3.88 (dd, 1H); 4.00–4.23 (m, 4H); 4.34 (dd, 1H); 4.58 (t, 1H); 7.59 (dd, 1H); 7.76 (d, 1H); 7.95 (dd, 1H); 8.25 (d, 1H).

The starting materials were prepared as follows:

To a solution of 4-acetylthio-1-(4-nitrobenzyloxy-carbonyl)- 2-carboxypyrrolidine (1.85 g; 5mM) in dichloromethane (20 ml) was added oxalylchloride (0.53 ml; 6 mM). A few drops of DMF were added to catalyse the reaction. The mixture was stirred for 1 hour. In the meantime, to a solution of 3-aminobenzoic acid (1.35 g, 10 mM) in dichloromethane (20 ml) was added diisopropylethylamine (5.2 ml, 30 mM). This solution was cooled to 0° C. and stirred while the solution of the acid chloride (prepared above) was added from a syringe at such a rate as to keep the temperature below 10° C. When the addition was complete the mixture was stirred for a further 30 minutes without cooling and then evaporated to dryness. The residue was partitioned between ethyl acetate (200 ml) and hydrochloric acid (2M, 100 ml). The ethyl acetate layer was separated and washed successively with water (50 ml), saturated brine (50 ml) and then dried over magnesium sulphate and evaporated to give an oily solid (2.3 g). This was recrystallised from isopropanol (30 ml) to give the title compound as a white crystalline solid (1.6 g, m.p. 187°–190° C.).

NMR δ(DMSO-d$_6$): 1.97 (m, 1H); 2.30 (s,3H; 2.80 (m, 1H); 3.39 (m, 1H); 4.04 (m,2H); 4.99 (dd,1H); 5.20 (dd,2H); 7.39 (dd, 1H); 7.56 (d,2H); 7.63 (m, 1H); 7.78 (m, 1H); 8.04 (d,2H); 8.16 (m, 1H); 9.83 (s,1H).

To a solution of (2S,4S)-4-acetylthio-1-(4-nitrobenzyloxycarbonyl)- 2-(3-carboxyphenylcarbamoyl)pyrrolidine (0.49 g, 1 mM) in dichloromethane (10 ml) was added oxalyl chloride (0.20 ml. 1.1 mM) and dimethylformamide (2–3 drops). After 1 hour a further amount of oxalyl chloride (0.20 ml, 1.1 mM) and DMF (2–3 drops) were added and the mixture stirred for a further hour. The solution was evaporated to leave a yellow gum. The gum was dissolved in dichloromethane (10 ml) and added to a suspension of 4-nitrobenzyl 2-aminoethanoate hydrochloride salt (0.30 g, 1.2 mM) and N-methylmorpholine (0.27 ml, 2.4 mM) in dichloromethane (10 ml). After 17 hours the mixture was diluted with dichloromethane (80 ml), washed with water (20 ml), brine (20 ml) and dried (MgSO$_4$). Purification by flash chromatography through silica using a gradient of dichloromethane to ethyl acetate as eluent gave (2S,4S)-4-acetylthio-1-(4-nitrobenzyloxycarbonyl)-2-(3-(4-nitrobenzyloxycarbonylmethylaminocarbonyl)phenylcarbamoyl)pyrrolidine (380 mg).

NMR δ: 2.25–2.45 (br m+s, 4H); 2.50–2.70 (br m, 1H); 3.40–3.50 (m, 1H); 4.00 (q, 1H); 4.10–4.35 (m, 3H); 4.45–4.55 (br m, 1H); 5.25–5.40 (m, 4H); 7.20 (brs, 1H); 7.40–7.70 & 8.20–8.30 (complicated broad peaks+doublets, 11H).

A solution of 4-nitrobenzyl (1R,5R,6S,8R)-6-(1-hydroxyethyl)- 1-methyl-2-diphenylphosphoryloxycarbapenem-3-carboxylate (340 mg, 0.56 mM) in acetonitrile (5 ml) and dichloromethane (2 ml) was purged with argon and cooled in an ice bath. To this was added ethyldiisopropylamine (0.30 ml, 1.68 mM), then a solution of 1-(4-nitrobenzyloxycarbonyl)-2-(3-allyloxycarbonylmethylamino-carbonylphenylcarbamoyl)pyrrolidin- 4-ylthiol (0.37 g, 0.56 mM) [the thiol was generated from the acetylthio compound by the method of Example 1. In the course of this reaction, which was carried out in allyl alcohol, the 4-nitrobenzyl ester function exchanged to give the allyl ester] in acetonitrile (5 ml). The mixture was stood at 5° C. for 17 hours, the solvent removed and the yellow gum purified by flash chromatography on silica eluting with a gradient from dichloromethane to ethyl acetate to acetonitrile, giving 4-nitrobenzyl (1R,5R, 6S,8R,2'S,4'S)-2-(1-(4-nitrobenzyloxycarbonyl)-2(3-allyloxycarbonylmethylaminocarbonylphenylcarbamoyl)pyrrolidin- 4-ylthio)-6-(1-hydroxyethyl)-1-methylcarbapenem-3-carboxylate as a yellow solid (310 mg).

NMR δ: 1.24 (d, 3H); 1.35 (d, 3H); 2.2–3.0 (br m, 2H); 3.23–3.36 (m, 2H); 3.4–3.75 (br m, 1H); 3.76–3.90 (br m, 1H); 3.97 (dd, 1H); 4.20–4.33 (m, 4H); 4.45–4.60 (m, 1H); 4.61–4.70 (m, 2H); 4.90–5.50 (m, 6H); 5.85 (m, 1H); 6.85–7.05 (br s, 1H); 7.30–8.25 (complex pattern of broad peaks, doublets & double doublets, 12H).

EXAMPLE 8

(1R,5S,6S,8R,2'S,4'S)-2-(2-( 3-Carboxymethoxymethylphenyl-carbamoyl)pyrrolidin- 4-ylthio)-6-(1-hydroxyethyl)-1-methylcarbapenem-3carboxylic acid, disodium salt was prepared from the corresponding allyl protected compound by the method described in example 1, except that DMF was replaced by DHSO, and crude product was sufficiently pure for use without chromatography.

NMR (DHSO-d$_6$/CD$_3$COOD): δ1.19 (d, 6H); 1.97 (m, part obscured, 1H); 2.88 (m, 1H); 3.17 (dd, 1H); 3.25 (dd, 1H); 3.40 (dt, 1H); 3.71 (dd, 1H); 3.93 (quintet, 1H); 3.96 (m, 1H); 4.07 (s, 2H); 4.22 (dd, 1H); 4.35 (t, 1H); 4.56 (s, 2H); 7.10 (d, 1H); 7.33 (t, 1H); 7.57–7.63 (m, 2H).

MS (+ve FAB): 542 (MH)$^+$ (mono Na salt); 564 (MH)$^+$ (di Na salt).

The starting materials were prepared as follows:
t-Butyl 3-nitrobenzyloxyacetate 3-Nitrobenzyl alcohol (5 g, 32.6 mM) was dissolved in DMF (200 ml) and cooled to 5°. Sodium hydride (60% in oil, 1.57 g, 39.2 mM) was added to the stirred solution in portions over 30 minutes, and the mixture cooled to −20°. t-Butyl bromoacetate (5.27 ml, 32.6 mM) was run in dropwise, and the mixture allowed to warm to ambient temperature overnight. Solvent was evaporated, the residue treated with water, and organics extracted into ethyl acetate. The combined organic layers were washed with water and brine, and dried over MgSO$_4$. Crude product was purified by chromatography on silica, eluting with a gradient from hexane/dichloromethane (95:5) to dichloromethane, to give t-butyl 3-nitrobenzyloxyacetate (7.71 g, 88%).

NMR (CDCl$_3$): δ1.50 (s, 9H); 4.06 (s, 2H); 4.71 (s, 2H); 7.53 (t, 1H); 7.74 (d, 1H); 8.16 (dm, 1H); 8.25 (t, 1H).

MS (CI): 285 (M+NH$_4$)$^+$.
3-Nitrobenzyloxyacetic acid t-Butyl 3-nitrobenzyloxyacetate (5 g, 18.7 mM) was dissolved in formic acid (50 ml) and stirred at ambient temperature for 48 hours. Solvents were removed to give 3-nitrobenzyloxyacetic acid (3.9 g, 98%). NMR (DMSO-d$_6$): δ4.15 (s, 2H); 4.69 (s, 2H); 7.66 (t, 1H); 7.81 (d, 1H); 8.13–8.22 (m, 2H); 12.73 (br, 1H).

MS (EI): 211M$^+$.

3-Nitrobenzyloxyacetic acid was allylated using the method described in example 1, using 3-nitrobenzyloxyacetic acid in place of 3-nitrocinnamic acid, to give allyl 3-nitrobenzyloxyacetate.

NMR (CDCl$_3$): δ4.21 (s, 2H); 4.69 (dt, 2H); 4.74 (s, 2H); 5.25–5.40 (m, 2H); 5.85–6.05 (m, 1H); 7.53 (t, 1H); 7.29 (d, 1H); 8.17 (dm, 1H); 8.25 (br s, 1H).

MS (CI): 252 (MH)$^+$; 280 (M+C$_2$H$_5$)$^+$.

Allyl 3-nitrobenzyloxyacetate was reduced by the method described in example 1 using allyl 3-nitrobenzyloxyacetate in place of allyl 3-nitrocinnamate, to give allyl 3-aminobenzyloxyacetate.

NMR (CDCl$_3$): δ3.67 (br, 2H): 4.11 (s, 2H); 4.55 (s, 2H); 4.68 (dt, 2H); 5.23–5.38 (m, 2H); 5.84–6.03 (m, 1H); 6.62 (dm, 1H); 6.70 (m, 2H); 7.12 (t, 1H).

MS (CI): 222 (MH)$^+$; 239 (H+NH$_4$)$^+$.

Allyl 3-aminobenzyloxyacetate was condensed with (2S, 4S)-4-acetylthio- 1-allyloxycarbonyl-2-carboxypyrrolidine by the method described in example 3 for allyl 3-aminophenoxyacetate, except that crude product was purified by chromatography on silica, using a gradient from di-chloromethane to dichloromethane/diethyl ether (85:15), to give (2S,4S)-4-acetylthio-1-allyloxycarbonyl-2-( 3(allyloxycarbonylmethoxymethyl)phenylcarbamoyl)pyrrolidine.

NMR (CDCl$_3$): δ2.33 (s, 3H); 2.58 (br, 2H); 3.39 (dd, 1H); 4.02 (quintet, 1H); 4.13 (s overlapping m, 3H); 4.54 (t, 1H); 4.62 (s, 2H); 4.68 (dm, 4H); 5.21–5.39 (m, 4H); 5.84–6.03 (m, 2H); 7.12 (d, 1H); 7.31 (t, 1H); 7.52 (m, 2H); 9.04 (br, 1H).

MS (+ve FAB): 477 (MH)⁺; 499 (M+Na)⁺.

(2S,4S)-4-Acetylthio-1-allyloxycarbonyl-2-( 3-(allyloxycarbonylmethoxymethyl)phenylcarbamoyl)pyrrolidine was deacetylated and condensed with allyl (1R,5R,6S,8R)-6-(1-hydroxyethyl)-1-methyl- 2-diphenylphosphoryloxycarbapenem-3-carboxylate by the method described in example 1 for (2S,4S)-4-acetylthio-1-allyloxycarbonyl-2-(3-(E- 2-carboxy-1-ethenyl)phenylcarbamoyl)pyrrolidine, except that purification by medium pressure chromatography used a gradient elution from dichloromethane to ethyl acetate, to give allyl (1R,5S,6S,8R,2'S,4'S)-2-(1-allyloxycarbonyl-2-(3-allyloxycarbonylmethoxymethylphenyl-carbamoyl)pyrrolidin- 4-ylthio)-6-(1-hydroxyethyl)-1-methylcarbapenem-3carboxylate.

NMR (CDCl₃): δ1.24 (d, 3H); 1.35 (d, 3H); 2.60 (br, 2H); 3.24 (dd overlapping m, 2H); 3.45 (br, 1H); 3.79 (quintet, 1H); 4.04 (dd, 1H); 4.13 (s, 2H); 4.24 (dd overlapping m, 2H); 4.51 (t, 1H); 4.63, 4.65–4.75 (s overlapping m, 8H); 5.20–5.44 (m, 6H); 5.86–6.02 (m, 3H); 7.13 (dm, 1H); 7.31 (t, 1H); 7.52 (m, 2H); 8.80 (br, 1H).

MS (+ve FAB): 684 (MH)⁺; 706 (M+Na)⁺.

EXAMPLE 9

(1R,5S,6S,8R,2'S,4'S)-2-(2-( 3-Carboxymethylthiophenyl-carbamoylpyrrolidin- 4-ylthio)-6-(1-hydroxyethyl)-1-methylcarbapenem-3carboxylic acid, disodium salt was prepared from the corresponding allyl protected compound by the method described in example 1, except that DMF was replaced by DMSO, and crude product was sufficiently pure for use without chromatography.

NMR (DMSO-d₆/CD₃COOD): δ1.14 (d, 3H); 1.18 (d, 3H); 1.80 (m, part obscured, 1H); 2.74 (dt, 1H); 296 (dd, 1H); 3.21 (dd, 1H); 3.38 (dt, 1H); 3.53 (dd, 1H); 3.75 (2×s, overlapping m, 3H); 3.99 (quintet, 1H); 4.10 (t, 1H); 4.17 (dd, 1H), 7.06 (d, 1H); 7.27 (t, 1H); 7.45 (dm, 1H); 7.64 (t, 1H).

MS (+ve FAB): 544 (MH)⁺ (mono Na salt); 566 (MH)⁺ (di Na salt).

The starting materials were prepared as follows:
Allyl 3-nitrophenylthioacetate

3-Nitrophenyl disulfide (5 g, 16.2 mM) was stirred in THF (125 ml), sodium borohydride (1.53 g, 40.5 mM) added, and the mixture heated to 50°. Methanol (12.5 ml) was added slowly to the stirred solution over 1 hour, after which the mixture was cooled to ambient temperature, and allyl chloroacetate (3.76 ml, 32.4 mM) run in. Stirring was continued for 3 hours, acetone (2 ml) was added, and stirring continued 5 minutes. The mixture was diluted with ethyl acetate, extracted with NaHCO₃ solution, washed with brine, and dried (MgSO₄), to give allyl 3-nitrophenylthioacetate (7.65 g, 93%).

NMR (CDCl₃): δ3.75 (s, 2H); 4.63 (dt, 2H); 5.21–5.37 (m, 2H); 5.78–5.98 (m, 1H); 7.46 (t, 1H); 7.71 (dm, 1H); 8.08 (dm, 1H); 8.24 (t, 1H).

MS (CI): 253 (M+NH₄)⁺.

Allyl 3-nitrophenylthioacetate was reduced by the method described in example 1 using allyl 3-nitrophenylthioacetate in place of allyl 3-nitrocinnamate, to give allyl 3-aminophenylthioacetate.

NMR (CDCl₃): δ3.65 (s overlapping br, 4H); 4.61 (dt, 2H); 5.19–5.36 (m, 2H); 5.78–5.98 (m, 1H); 6.53 (dm, 1H); 6.72-6.80 (m, 2H); 7.07 (t, 1H).

MS (CI): 224 (MH)⁺; 252 (M+C₂H₅)⁺.

Allyl 3-aminophenylthioacetate was condensed with (2S, 4S)-4-acetylthio- 1-allyloxycarbonyl-2-carboxypyrrolidine by the method described in example 3 for allyl 3-aminophenoxyacetate, except that crude product was purified by chromatography on silica, using a gradient from dichloromethane to dichloromethane/diethyl ether (4:1), to give (2S,4S)-4-acetylthio-1-allyloxycarbonyl-2-( 3-(allyloxycarbonylmethylthio)phenylcarbamoyl)pyrrolidine.

NMR (CDCl₃): δ2.33 (s, 3H); 2.56 (br, 2H); 3.38 (dd, 1H); 3.68 (s, 2H); 4.04 (quintet, 1H); 4.13 (dd, 1H); 4.53 (t, 1H); 4.60—4.67 (m, 4H); 5.20–5.38 (m, 4H); 5.79–6.03 (m, 2H); 7.15 (t, 1H); 7.25 (dm, 1H); 7.38 (dm, 1H); 7.63 (t, 1H); 9.11 (br, 1H).

MS (+ve FAB): 479 (MH)⁺; 501 (M+Na)⁺.

(2S,4S)-4-Acetylthio-1-allyloxycarbonyl-2-( 3-(allyloxycarbonylmethylthio)phenylcarbamoyl)pyrrolidine was deacetylated and condensed with allyl (1R,5R,6S,8R)-6-(1-hydroxyethyl)-1-methyl- 2-diphenylphosphoryloxycarbapenem-3-carboxylate by the method described in example 1 for (2S,4R)-4-acetylthio-1-allyloxycarbonyl-2-(3-(E- 2-carboxy-1-ethenyl)phenylcarbamoyl)pyrrolidine, except that purification by medium pressure chromatography used a gradient elution from dichloromethane to ethyl acetate, to give allyl (1R,5S,6S,8R,2'S,4'S)-2-(1-allyloxycarbonyl-2-( 3-allyloxycarbonyl-methylthiophenylcarbamoyl)pyrrolidin-4-ylthio)-6-(1-hydroxyethyl)- 1-methylcarbapenem-3-carboxylate.

NMR (CDCl₃): δ1.24 (d, 3H); 1.36 (d, 3H); 2.63 (br, 2H); 3.26 (dd overlapping quintet, 2H); 3.48 (br, 1H); 3.69 (s, 2H); 3.80 (quintet, 1H); 4.01 (dd, 1H); 4.26 (dd overlapping quintet, 2H); 4.51 (t, 4.58–4.81 (m, 6H); 5.19–5.45 (m, 6H); 5.80–6.01 (m, 3H); 7.14 (d, 1H); 7.25 (t, 1H); 7.42 (d, 1H); 7.68 (br s, 1H); 8.91 (br, 1H).

MS (+ve FAB): 686 (MH)⁺; 708 (M+Na)⁺.

EXAMPLE 10

(1R,5S,6S,8R,2'S,4'S)-2-(2-Carboxymethylcarbamoyl-5-thienylcarbamoyl)-pyrrolidine-4-ylthio)-6-(1-hydroxyethyl)-1-methylcarbapenem-3-carboxylic acid (Na Salt).

A solution of 4-nitrobenzyl (1R,5S,6S,8R,2'S,4'S)-2-(1-( 4-nitrobenzyloxycarbonyl)-2-(2-carboxymethylcarbamoyl-5-thienyl-carbamoyl)pyrrolidin- 4-ylthio)-6-(1-hydroxyethyl)-1-methylcarbapenem-3carboxylate (165 mg, 0.194 mmol) in water (10 ml), ethyl acetate (10 ml) and sodium bicarbonate (pH adjusted to 7.5) was hydrogenated at atmospheric pressure in presence of Pd/C (10%) (165 mg). The reaction was followed by analytical HPLC. The catalyst was filtered off and the aqueous solution concentrated, and purified by preparative HPLC (Nucleosil C-18), eluting with water. Freeze drying the appropriate fractions gave the title compound (27 mg, 25%).

NMR: (DMSO-$d_6$+AcOD-$d_4$): δ1.18 (2d, 6H); 1.80 (m, 1H); 2.60 (m, 1H); 2.70 (m, 1H); 3.2 (m, 1H); 3.30–3.42 (m, 2H); 3.60 (m, 1H); 3.90–4.04 (m, 2H); 4.14 (dd, 1H); 6.89 (d, 1H); 7.54 (d, 1H).

The starting material was prepared as follows:

5-Nitro-2-thiophenecarboxylic acid

2-Thiophenecarboxylic acid (6.4 g, 50 mM) was suspended in acetic anhydride (15 ml) and fuming nitric acid (16 ml) in glacial acetic acid (25 ml) added slowly over 1 hour with stirring, while keeping the temperature of the reaction mixture below 30° C. The reaction mixture was stirred at ambient temperature for 2 hours. The product was purified by subjecting to chromatography (470 ml) on HP20SS resin using methanol/(water +1% acetic acid): as eluant. The pure title compound was obtained together with a mixture of 4- and 5-nitrothiophene-2-carboxylic acid.

NMR (CDCl$_3$): δ7.65 (d, 1H); 7.88 (d, 1H).

Allyl 5-Nitro-2-thiophenecarboxylate

To a solution of 5-nitro-2-thiophenecarboxylic acid (20 g, 0.11 mol) in DMF (140 ml) were added sequentially allyl bromide (40 ml, 0.46 mol) and triethylamine (64 ml, 0.46 mol) with cooling to maintain the temperature of the reaction mixture below 30° C. After addition of the reagents, the reaction mixture was stirred for 3 hours at ambient temperature and then diluted with ethyl acetate. The solid which precipitated was filtered off, the filtrate washed with water, washed with saturated aqueous solution of sodium chloride, dried over MgSO$_4$ and concentrated. The residue was purified by chromatography on silica gel using a mixture of CH$_2$Cl$_2$ —petroleum ether (3:7) as eluent to give the title compound as a white solid (8.8 g, 38%).

NMR (CDCl$_3$): δ4.84 (d, 2H); 5.36–5.45 (m, 2H); 6.00 (m, 1H); 7.71 (d, 1n); 7.88 (d, 1n).

Allyl 5-amino-2-thiophenecarboxylate

To a solution of allyl 5-nitro-2-thiophenecarboxylate (3.2 g, 15 mmol) in concentrated hydrogen chloride (35 ml) were added under cooling SnCl$_2$.H$_2$O (10.1 g, 45 mmol). The mixture was stirred for 3.5 hours at ambient temperature, diluted with ethyl acetate and basified to pH 10 with 5N NaOH. The organic layer was washed with water and a saturated aqueous solution of sodium chloride, dried over MgSO$_4$ and concentrated. The residue was purified by chromatography on silica gel using a mixture of ethyl acetate and petroleum ether (3:7) to give the title compound as a yellow oil (1.94 g, 72%).

NMR (CDCl$_3$): δ4.34 (br s, 2H); 4.73 (d, 2H); 5.23 (d, 1H); 5.36 (d, 1H); 5.99 (m, 1H); 6.09 (d, 1H); 7.48 (d, 1H).

(2S,4S)-1-(4-Nitrobenzyloxycarbonyl)-2-(2allyloxycarbonyl- 5-thienyl-carbamoyl)pyrrolidine-4-ylthioacetate.

To a solution of (2S,4S)-4-acetylthio-2-carboxy-1-(4-nitrobenzyloxycarbonyl)pyrrolidine (3.79 g, 10.3 mmol) in CH$_2$Cl$_2$ (12 ml) were added thionyl chloride (3.75 ml, 51.5 mmol) and DMF (0.055 ml). The mixture was stirred for 16 hours at ambient temperature, concentrated and the residual oil taken up in CH$_2$Cl$_2$-toluene and reevaporated. The residue was dried under vacuum and solubilised in CH$_2$Cl$_2$ (25 ml). To this solution cooled to 0° C. was added N-diisopropylethylamine (2.05 ml, 11.8 mmol) and a solution of allyl 5-amino-2-thiophenecarboxylate (1.9 g, 10.3 mmol). After 15 minutes at ambient temperature, the solvent was evaporated and the residue taken up in a mixture of water and ethyl acetate. The organic layer was dried over MgSO$_4$ and evaporated to dryness. The residue was purified by chromatography on silica gel using a mixture of CH$_2$CL$_2$-ether (9:1) to give the title compound as a yellow foam (4.68 g, 85%).

NMR (DMSO-$d_6$+AcOD-$d_4$): δ2.33 (s, 3H); 2.80 (m, 1H); 3.38 (m, 1H); 4.00–4.15 (m, 2H); 4.52 (m, 2H); 4.77 (d, 2H); 5.02–5.42 (m, 4H); 6.00 (m, 1H); 6.77 (m, 1H); 7.45 (m, 1H); 7.60–7.68 (m, 2H); 7.95 (m, 1H); 8.23 (m, 1H).

(2S,4S)-1-(4-Nitrobenzyloxycarbonyl)-2-(2-carboxy- 5thienylcarbamoyl)-pyrrolidin-4-ylthioacetate.

A solution of (2S,4R)-1-(4-nitrobenzyloxycarbonyl)-2-(2-allyloxycarbonyl-5-thienylcarbamoyl)pyrrolidin-4-ylthioacetate (5.33 g, 10 mmol) in CH$_2$Cl$_2$ (15 ml) and ethyl acetate (15 ml) was treated with P(Ph)$_3$ (0.26 g, 1 mmol), potassium 2-ethylbenzoate (0.47M in ethyl acetate, 23.4 ml, 11 mmol) and Pd(PPh$_3$)$_4$ (0.25 g) at ambient temperature. The reaction was followed by HPLC. After 3 hours, the mixture was diluted with ethyl acetate, the precipitate filtered, washed with ether and dried. This solid was dissolved in water, acidified with HCl (2N), and the free acid extracted with ethyl acetate, dried over MgSO$_4$ and the solvent evaporated to give title compound (4.95 g, 100%).

NMR: (DMSO-$d_6$+CF$_3$CO$_2$D): δ1.95 (m, 1H); 2.33 (s, 3H); 2.78 (m, 1H); 3.38 (m, 1H); 3.98–4.1 (m, 2H); 4.52 (m, 1H); 5.03–5.33 (m, 2H); 6.72–6.76–7.52–7.54 (4d, 2H); 7.46–8.25 (4d, 4H).

(2S,4S)-1-(4-Nitrobenzyloxycarbonyl-2-(2-carboxymethylcarbamoyl- 5-thienylcarbamoyl)pyrrolidin-4-ylthioacetate.

A solution of (2S,4S)-1-(4-nitrobenzyloxycarbonyl)-2-(2-carboxy- 5-thienylcarbamoyl)pyrrolidin-4-ylthioacetate (10 g, 2.03 mmol) in CH$_2$Cl$_2$ (50 ml) was treated with oxalyl chloride (0.4 ml, 4.56 mmol) and DMF (20 mg). The mixture was stirred for 2 hours, evaporated, dissolved in a mixture of CH$_2$Cl$_2$: toluene 1:1 (10 ml) and evaporated. The residual oil was dried for 1 hour under vacuum and solubilized in anhydrous CH$_2$Cl$_2$ (50 ml). This solution was added to a solution of glycine (0.2 g, 2.66 mmol), diisopropylethylamine (1.3 ml, 8 mmol) and trimethylsilylchloride (1 ml, 8 mmol) in anhydrous CH$_2$Cl$_2$ (50 ml) under argon at 0° C. The mixture was stirred at ambient temperature for 1 hour and the solvent evaporated. The residue was taken up in 2N HCl, extracted with ethyl acetate, washed with water (three times) and dried over MgSO$_4$ to give the title compound (1.06 g, 95%).

NMR (DMSO-$d_6$+CF$_3$CO$_2$D): δ1.95 (m, 1H); 2.33 (s, 3H); 2.78 (m, 1H); 3.36 (m, 1H); 3.90 (s, 2H); 3.95–4.18 (m, 2H); 4.54 (m, 1H); 5.04–5.34 (m, 2H); 6.72–7.58 (2m, 2H); 7.46–8.25 (4d, 4H).

(2S,4S),1-(4-Nitrobenzyloxycarbonyl)-2-(2-carboxymethylcarbamoyl- 5-thienylcarbamoyl)pyrrolidin-4-ylthiol.

(2S,4S)-1-(4-Nitrobenzyloxycarbonyl)-2-(2-carboxymethyl-carbamoyl- 5-thienylcarbamoyl)pyrrolidin-4-ylthioacetate (0.55 g, 1 mmol) was solubilized in CH$_2$Cl$_2$ (5 ml) and dry methanol (10 ml) and treated with a solution of sodium hydroxide (1N) (2 ml, 2 mmol). The progress of the reaction was monitored by tlc. After 2 hours the pH of solution was adjusted to 7 with HCl (IN) and evaporated to dryness. The crude thiol was dissolved in DMF (5 ml) and used in the next step without further purification. 4-Nitrobenzyl (1R,5S,6S, 8R,2'S,4'S)-2-(1-( 4-nitrobenzyloxycarbonyl- 2-(3-hydroxy-5-carboxy-2-thienylcarbamoyl)pyrrolidin-4ylthio)-6-( 1-hydroxyethyl)- 1-methylcarbapenem-3-carboxylate.

A solution of 4-nitrobenzyl (1R,5R,6S,8R)-6-(1-hydroxyethyl)-1-methyl-2-diphenylphosphoryloxycarbapenem-3-carboxylate (594 mg, 1 mmol) in DMF (5 ml) under argon was treated with (2S,4S)-1-( 4-nitro-benzyloxycarbonyl)-2-(2-carboxymethylcarbamoyl-5-thienylcarbamoyl)-pyrrolidin- 4-ylthiol (from previous step), diisopropylethylamine (0.08 ml, 0.5 mmol), tributylphosphine (250 μl, 1 mmol) and water (20 μl, 1 mmol), for 12 hours at 4° C. temperature. The mixture was then purified by subjecting to chromatography on a HP20SS column, eluting with a gradient of acetonitrile water to give title compound (175 mg, 21%).

NMR: (DMSO-d$_6$+AcOH-d$_4$): δ1.18 (2d, 6H); 1.92 (m, 1H); 2.83 (m, 1H); 3.31 (m, 1H); 3.38 (m, 1H); 3.59 (m, 1H); 3.84–3.94 (m, 2H); 3.96–4.06 (m, 2H); 4.11–4.36 (m, 2H); 4.53 (m, 1H); 5.02-5.48 (m, 4H); 6.66–8.31 (m, 1OH).

We claim:

1. A compound of the formula (I):

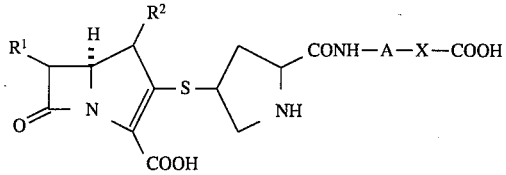

or a pharmaceutically acceptable salt or in vivo hydrolysable ester thereof wherein:

A is a group of the formula (IA) or (IB)

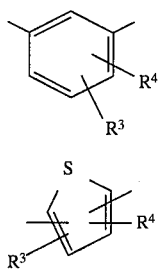

$R^1$ is 1-hydroxyethyl, 1-fluoroethyl or hydroxymethyl;
$R^2$ is hydrogen or $C_{1-4}$alkyl;
$R^3$ and $R^4$ are the same or different and are selected from the group consisting of hydrogen, halo, cyano, $C_{1-4}$alkyl, nitro, hydroxy, carboxy, $C_{1-4}$alkoxy, $C_{1-4}$alkoxycarbonyl, carbamoyl, $C_{1-4}$alkylcarbamoyl, di-$C_{1-4}$alkylcarbamoyl, trifluoromethyl, and $C_{3-4}$alkenyloxy;
X is alkanediyl containing 1–6 carbon atoms optionally interrupted by the function O, S(O)$_x$, wherein x is zero, one or two, —CONR$^5$— or —NR$^5$— wherein R$^5$ is hydrogen or $C_{1-4}$alkyl;
or X is alkenediyl containing 2–6 carbon atoms optionally interrupted by the function O, S(O)$_x$ or —NR$^5$— wherein x and R$^5$ are as hereinbefore defined; with the provisos that:
  i) the interrupting function, O,S(O)$_x$,NR$^5$,—CONR$^5$—, may be directly linked to the ring A, but is not directly linked to the —COOH function or to any carbon-carbon double bond in X; and
  (ii) when the interrupting function is —SO— or —SO$_2$— it is not β to the COOH function or δ if there is an intervening carbon-carbon double bond in X.

2. A compound according to claim 1 wherein R$^1$ is 1-hydroxyethyl.

3. A compound according to either claim 1 or claim 2 of the formula (IV):

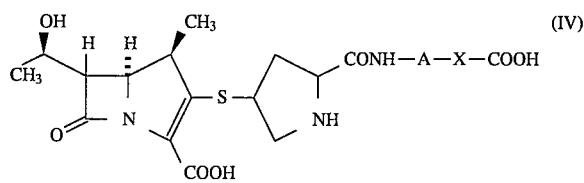

wherein A and X are as defined in claim 1.

4. A compound according to claim 3 wherein X is methylene, ethylene, oxymethylene, vinylene, methyloxymethylene or thiomethylene.

5. A compound according to claim 3 wherein R$^3$ and R$^4$, in A, are independently selected from hydrogen, halo, cyano, $C_{1-4}$alkyl, nitro, hydroxy, carboxy, $C_{1-4}$alkoxy, carbamoyl, $C_{1-4}$alkylcarbamoyl, di-$C_{1-4}$alkylcarbamoyl, trifluoromethyl and $C_{3-4}$alkenyloxy.

6. A compound selected from the group consisting of
(1R,5S,6S,8R,2'S,4'S)-2-(2-(3-(E- 2-carboxy-1-ethenyl)phenylcarbamoyl)pyrrolidin-4-ylthio)-6-(1-hydroxyethyl)-1-methylcarbapenem-3-carboxylic acid,
(1R,5S,6S,8R,2'S,4'S)-2-(2-(3-(E- 2-carboxy-1-ethenyl)-6-hydroxyphenylcarbamoyl)pyrrolidin- 4-ylthio)-6-(1-hydroxyethyl)-1-methylcarbapenem- 3-carboxylic acid,
(1R,5S,6S,8R,2'S,4'S)-2-(2-( 3-carboxymethoxyphenylcarbamoyl)pyrrolidin- 4-ylthio)-6-(1-hydroxyethyl)-1-methylcarbapenem-3-carboxylic acid,
(1R,5S,6S,8R,2'S,4'S)-2-(2-(3-carboxyethylphenylcarbamoyl)pyrrolidin- 4-ylthio)-6-(1-hydroxyethyl)-1-methylcarbapenem-3-carboxylic acid,
(1R,5S,6S,8R,2'S,4'S)-2-(2-(5-carboxymethyl- 2-hydroxyphenylcarbamoyl)pyrrolidin- 4-ylthio)-6-(1-hydroxyethyl)-1-methylcarbapenem-3-carboxylic acid,
(1R,5S,6S,8R,2'S,4'S)-2-(2-( 3-carboxymethylphenylcarbamoyl)pyrrolidin- 4-ylthio)-6-(1-hydroxyethyl)-1-methylcarbapenem-3-carboxylic acid,
(1R,5S,6S,8R,2'S,4'S)-2-(2-( 3-carboxymethylaminocarbonylphenylcarbamoyl)pyrrolidin- 4-ylthio)-6-(1-hydroxyethyl)-1-methylcarbapenem-3-carboxylic acid,
(1R,5S,6S,8R,2'S,4'S)-2-(2-( 3-(carboxymethoxymethyl)phenylcarbamoyl)pyrrolidin- 4-ylthio)-6-(1-hydroxyethyl)-1-methylcarbapenem-3-carboxylic acid,
(1R,5S,6S,8R,2'S,4'S)-2-(2-( 3-(carboxymethylthio)phenylcarbamoyl)pyrrolidin- 4-ylthio)-6-(1-hydroxyethyl)-1-methylcarbapenem-3-carboxylic acid, and
(1R,5S,6S,8R,2'S,4'S)-2-(2-( 2-carboxymethylcarbamoyl-5-thienylcarbamoyl)pyrrolidin- 4-ylthio)-6-(1-hydroxyethyl)-1-methylcarbapenem-3-carboxylic acid,
or a pharmaceutically acceptable salt thereof.

7. A pharmaceutical composition which comprises a compound according to claim 1 and a pharmaceutically acceptable carrier.

8. A method of treatment of a bacterial infection by administering an antibacterially effect amount of a compound of the formula (I) as defined in claim 1 to a patient in need thereof.

* * * * *